United States Patent [19]

Knodle et al.

[11] Patent Number: 4,859,858
[45] Date of Patent: Aug. 22, 1989

[54] GAS ANALYZERS

[75] Inventors: Daniel W. Knodle, Seattle; Leslie E. Mace, Mercer Island; Lawrence L. Labuda, Issaquah, all of Wash.

[73] Assignee: Cascadia Technology Corporation, Redmond, Wash.

[21] Appl. No.: 24,770

[22] Filed: Mar. 11, 1987

Related U.S. Application Data

[63] Continuation-in-part of Ser. No. 938,030, Dec. 4, 1986, abandoned.

[51] Int. Cl.[4] ............................................. H05B 3/26
[52] U.S. Cl. ............................ 250/504 R; 250/493.1; 219/553; 219/543
[58] Field of Search ................ 250/504 R, 493.1, 343; 330/260; 307/296.3; 219/553, 543

[56] References Cited

U.S. PATENT DOCUMENTS

| | | | |
|---|---|---|---|
| 2,286,985 | 6/1942 | Hanson | 356/437 |
| 2,758,215 | 8/1956 | Skarstrom | 250/43.5 |
| 3,694,624 | 9/1972 | Buchta | 219/358 |
| 3,745,349 | 7/1973 | Liston | 250/218 |
| 3,793,525 | 2/1974 | Burch et al. | 250/343 |
| 3,811,776 | 5/1974 | Blau, Jr. | 356/51 |
| 3,821,553 | 6/1974 | French | 250/339 |
| 3,860,344 | 1/1975 | Garfunkel | 356/51 |
| 3,875,413 | 4/1975 | Bridgham | 250/492 |
| 3,895,630 | 7/1975 | Bachman | 128/2.07 |
| 3,910,551 | 10/1975 | Ragsdale et al. | 128/2.07 |
| 3,922,551 | 11/1975 | Williams | 250/343 |
| 3,939,348 | 2/1976 | Barrett | 250/339 |
| 3,974,360 | 8/1976 | Panzarino | 219/543 |
| 3,987,303 | 10/1976 | Stoft et al. | 250/343 |
| 4,008,394 | 2/1977 | Risgin et al. | 250/345 |
| 4,011,859 | 3/1977 | Frankenberger | 128/2 C |
| 4,050,832 | 9/1977 | Frankenberger | 356/186 |
| 4,067,320 | 1/1978 | Olsson et al. | 128/2 C |
| 4,084,096 | 4/1978 | Edwards | 250/504 |
| 4,103,174 | 7/1978 | McClatchie et al. | 250/493 |
| 4,153,837 | 5/1979 | Ross | 250/343 |
| 4,163,899 | 8/1979 | Burough | 250/343 |
| 4,180,734 | 12/1979 | Gedeon | 250/345 |
| 4,204,768 | 5/1980 | N'Guyen | 356/243 |
| 4,268,751 | 5/1981 | Fritzlen et al. | 250/343 |
| 4,333,724 | 6/1982 | Honma | 356/437 |
| 4,345,840 | 8/1982 | Goetz et al. | 356/407 |
| 4,371,785 | 2/1983 | Pedersen | 250/343 |
| 4,378,489 | 3/1983 | Chabinsky et al. | 219/543 |

(List continued on next page.)

FOREIGN PATENT DOCUMENTS

221839A1 5/1986 German Democratic Rep. .

Primary Examiner—Jack I. Berman
Attorney, Agent, or Firm—Hughes & Multer

[57] ABSTRACT

Gas analyzers of the non-dispersive infrared radiation type which are designed to measure the concentration of one gas in a mixture of gases containing that gas. A novel, electrically modulated, stable, thick film infrared radiation emitter is employed to emit a beam of collimated, focused energy; and two electrically biased detectors are preferably used so that a ratioed, error eliminating output signal can be supplied to the failsafe, signal processing circuitry of the analyzer. The latter, and a conventional analog-to-digital convertor, supply information to a microcomputer which: (1) turns the infrared radiation emitter on and off; (2) controls a heater which keeps the infrared radiation detectors at a constant, precise temperature; and (3) controls displays of a variety of information concerning the gas being measured and the status of the gas analyzer. The microcomputer also accepts ambient temperature, barometric pressure, and other compensation factors. Typically, a disposable airway adapter will be included in the gas analyzer to confine the mixture of gases being analyzed to a path having a transverse dimension of precise and specific length and to provide an optical path across that stream of gases between the infrared radiation emitter and the infrared radiation detectors. The emitter and detectors are incorporated in a transducer head which can be detachably fixed to the airway adapter.

20 Claims, 10 Drawing Sheets

U.S. PATENT DOCUMENTS

| | | | |
|---|---|---|---|
| 4,420,687 | 12/1983 | Martinez et al. | 250/343 |
| 4,423,739 | 1/1984 | Passaro et al. | 128/719 |
| 4,437,005 | 3/1984 | Ophoff et al. | 250/343 |
| 4,480,190 | 10/1984 | Burough et al. | 250/343 |
| 4,499,378 | 2/1985 | Miyatake et al. | 250/343 |
| 4,499,379 | 2/1985 | Miyatake et al. | 250/343 |
| 4,500,207 | 2/1985 | Maiden | 356/409 |
| 4,501,968 | 2/1985 | Ebi et al. | 250/343 |
| 4,522,204 | 6/1985 | Kurahashi et al. | 128/719 |
| 4,560,875 | 12/1985 | Crowder | 250/343 |
| 4,577,105 | 3/1986 | Krempl et al. | 250/343 |
| 4,590,374 | 5/1986 | Brewster | 250/338 |
| 4,591,701 | 5/1986 | Tokumaru | 219/543 |
| 4,596,931 | 6/1986 | Ehnholm et al. | 250/343 |
| 4,598,201 | 7/1986 | Fertig et al. | 250/343 |
| 4,618,771 | 10/1986 | Farren | 250/343 |
| 4,620,104 | 10/1986 | Nordal et al. | 250/493.1 |
| 4,644,141 | 2/1987 | Hagen et al. | 219/543 |

GAS ANALYZERS

CROSS REFERENCE TO RELATED APPLICATION

This application is a continuation-in-part of application No. 938,030 filed Dec. 4, 1986, by Daniel W. Knodle et al. and entitled GAS ANALYZERS, now abandoned.

TECHNICAL FIELD OF THE INVENTION

The present invention relates to novel, improved devices for measuring the amount of one gas in a mixture of gases. This gas is referred to hereinafter as the "selected gas," the "measured gas," or the "designated gas."

One important application of the invention at the present time is in the provision of capnometers for monitoring the amount of carbon dioxide in the breath of a medical patient. Why it is advantageous to do this has been extensively discussed in the patent and open literature and need not be repeated herein.

For the sake of convenience and clarity, the principles of our invention will be developed primarily by reference to that application of those principles discussed in the preceding paragraph. This, however, is not intended to limit the scope of our invention as defined in the appended claims.

BACKGROUND OF THE INVENTION

Our novel gas analyzers operate on the premise that the concentration of a designated gas in a mixture of gases can be measured by passing a particularized beam of infrared radiation through the mixture of gases and ascertaining the attenuation of the energy in a narrow band absorbable by the designated gas with a detector capable of generating an attenuation proportional electrical output signal.

Gas analyzers which similarly employ an infrared source and a detector for generating an electrical signal representing the attenuation of the emitted radiation by a designated gas in the mixture being analyzed have heretofore been proposed. Such devices are commonly referred to as utilizing non-dispersive infrared radiation.

Generation of a detector output signal of a high enough signal-to-noise ratio to be useful requires that the beam of attenuated infrared radiation falling on the detector of such an instrument be modulated. Heretofore, this has perhaps most commonly been accomplished by interposing a spinning wheel between the infrared radiation source and the detector. These wheels, commonly known as choppers, have a series of apertures spaced equally around their peripheries. Consequently, as the wheel rotates, the transmission of the attenuated beam of infrared radiation to the detector of the gas analyzer is alternately enabled and interrupted, typically at a frequency of less than one hundred cycles per second.

Gas analyzers of the character just described are disclosed in U.S. Pat. Nos.: 3,793,525 issued Feb. 19, 1974, to Bursch et al. for DUAL-CELL NON-DISPERSIVE GAS ANALYZER; 4,811,776 issued May 21, 1974, to Blau, Jr. for GAS ANALYZER; 3,987,303 issued Oct. 19, 1976, to Steft et al. for MEDICAL-ANALYTICAL GAS DETECTOR; 4,011,859 issued Mar. 15, 1977, to Frankenberger for METHOD FOR CONTINUOUSLY MEASURING THE $CO_2$ CONTENT IN BREATHING GAS; 4,204,768 issued May 27, 1980, to N'Guyen for GAS ANALYSERS OF THE SELECTIVE RADIATION ADSORPTION TYPE WITH A CALIBRATION CELL; 4,268,751 issued May 19, 1981, to Fritzlen et al. for INFRARED BREATH ANALYZER; and 4,371,785 issued Feb. 1, 1983, to Pedersen for METHOD AND APPARATUS FOR DETECTION OF FLUIDS and in A Reliable, Accurate $CO_2$ Analyzer for Medical Use, Solomon, HEWLETT-PACKARD JOURNAL, Sept. 1981, pages 3–21.

Gas analyzers with mechanical choppers such as those described in the just-cited patents have a number of drawbacks. They are bulky, heavy, and expensive; have moving parts, which is undesirable; and also have complex optical designs. They also tend to be less accurate than is desirable and to lack long-term stability.

Also, gas analyzers employing mechanical choppers are relatively fragile. For example, they will typically not work properly, if at all, after they are dropped.

Another heretofore proposed type of gas analyzer employiygn absorption of infrared radiation as a measure of gas concentration is disclosed in U.S. Pat. No. 3,745,349 issued July 10, 1973, to Liston for SINGLE PATH, DUAL SOURCE RADIANT ENERGY ANALYZER. The infrared radiation source of the Liston device includes wires which are heated by applying pulses of electrical current thereto, thus providing a modulated source of radiation.

While this scheme at least theoretically eliminates the need for a mechanical chopper, it unfortunately has several serious drawbacks. The wires Liston employs are spaced apart. Consequently, the infrared radiation is not uniformly emitted over the area embraced by those wires. As the wires heat up and cool down, their diameters change, affecting the stability of the radiation. The devices cannot be pulsed at frequencies greater than about 20–25 Hz whereas the desirable modulation frequency of the infrared radiation, at least for carbon dioxide, ranges from 40–100 Hz.

Still other patents dealing with pulsed infrared radiation sources are Nos. 3,922,551 issued Nov. 25, 1985, to Williams for DETECTION OF $CO_2$ IN A HYPERBARIC GASEOUS ENVIRONMENT; 4,084,096 issued Apr. 11, 1976, to Edwards for ELECTRICALLY ACTIVATED INFRARED SOURCE; 4,163,899 issued Aug. 7, 1979, to Burrough for METHOD AND APPARATUS FOR GAS ANALYSIS; and 4,480,190 issued Oct. 30, 1984, to Burrough et al. for NON-DISPERSIVE INFRARED GAS ANALYZER and in a paper entitled Introduction to the State of the Art Gas Sensors by Liston Edwards, Inc., Costa Mesa, Calif.

Williams discloses an infrared radiation emitter employing cyclic variations in gas pressure to modulate the emitted radiation. This scheme is complex and bulky, requires moving parts, and demands a large amount of power.

Burroughs and Burroughs et al. are also concerned with a modulation scheme which employs mechanical parts and requires a large power input. In addition, the scheme disclosed in those patents, which employs an incandescent bulb as a radiation source, is not capable of modulating the emitted radiation to an extent approaching that needed for accurate gas analysis.

Like Liston, Edwards and Liston Edwards employ heated wires as a source of infrared radiation. Their sources therefore have all of the above-discussed drawbacks of Liston's.

An infrared radiation emitter somewhat similar in appearance to those disclosed herein is the subject of U.S. Pat. No. 3,875,413 issued Apr. 1, 1985, to Bridgham for INFRARED RADIATION SOURCE. However, the Bridgham infrared radiation source differs from ours in that he employs a thin film rather than thick film source of infrared radiation. As a result, the Bridgham infrared radiation emitter is not capable of being modulated; and it would be difficult to produce in quantity.

SUMMARY OF THE INVENTION

We have now invented, and disclosed herein, certain new and novel gas analyzers employing non-dispersive infrared radiation to measure the concentration of a selected gas in a mixture of gases. These novel gas analyzers are free of the drawbacks of heretofore available instruments of the same general character.

In general, in our novel instruments, the infrared radiation is emitted from an also novel, thick film source and focused by a mirror on the mixture of gases being analyzed. After passing through that body of gases, the beam of infrared radiation is passed through a filter. That filter absorbs all of the radiation except for that in a narrow band centered on a frequency which is absorbed by the gas of concern in the mixture being analyzed. This narrow band of radiation, which typically extends ca. 190 angstroms to each side of the frequency on which the radiation is centered, is allowed to reach a detector which is capable of producing an electrical output signal proportional in magnitude to the magnitude of the infrared radiation impinging upon it.

Thus, the radiation in that band is attenuated to an extent which is proportional to the concentration of the designated gas in the mixture of gases being analyzed. The strength of the signal generated by the detector is consequently inversely proportional to the concentration of the designated gas and can be inverted to provide a signal indicative of that concentration.

In a typical instrument involving the principles of our invention, the analog detector output signal is converted to a digital form because digital control over the operation of the gas analyzer can be affected much more rapidly than would be the case if analog control were employed. The digital signal is processed in a microcomputer and displayed to show the instantaneous digital concentration of the gas of concern in the mixture being analyzed. Also, other information can be extracted from the signal and displayed. In medical applications of our invention such information includes minimum inspiration carbon dioxide and respiratory rate. This capability is a significant advantage of our invention. For example, with respect to medical applications of the invention, other parameters listed above are as important as instantaneous concentration of carbon dioxide in determining a patient's medical condition.

Our gas analyzers also feature a novel source for the infrared radiation. This source includes a thick film infrared radiation emitter. The emitter is composed of a film of an emissive, electrically resistive material on a substrate of a material possessing low thermal conductivity such as steatite or, less preferably, alumina.

Associated with this infrared radiation emitter is a novel power supply which applies pulses of electrical energy to the emissive film of the infrared radiation emitter at a frequency of 40–100 Hz. This modulation of the infrared radiation emitter is employed because the detectors we employ operate properly only if the infrared radiation falling on them is modulated; and modulation of the emitter makes it possible to provide a suitably modulated beam of radiation without employing moving parts.

The beam of infrared radiation from the thick film emitter is passed through the mixture of gases being analyzed. An attenuated beam emerges from this mixture and impinges on two juxtaposed infrared radiation detectors preferably made of a state-of-the-art material such as lead selenide. An optical filter which will transmit only a first narrow band of infrared radiation centered on a frequency absorbed by the gas of interest is placed in front of one of these detectors as discussed above. Therefore, the radiation impinging on that detector will be attenuated to an extent which is dependent upon the concentration of the designated gas in the mixture being analyzed. A second optical filter capable of transmitting infrared radiation in a second, similarly narrow band centered on a frequency which is not absorbed by the gas of interest is placed in front of the second infrared radiation detector.

Because of their juxtaposition, the infrared radiation reaching both detectors will, for all practical purposes, be attenuated equally by contamination along the optical path between the infrared radiation emitter and the detectors. Also, it will be equally affected by thermal drift and by any other minor instabilities in the infrared radiation emitter.

Consequently, by ratioing the signals generated by the two detectors, as is done in our novel instruments, the effect of foreign substances in the optical path between the infrared radiation emitter and detectors and the effect of any instabilities in the infrared radiation emitter can be eliminated.

Compensation is also made for variations in ambient temperature and pressure and for oxygen and nitrogen assumed to be present in the gas mixture in medical and other applications of our invention.

Lead selenide detectors are preferably employed in the novel gas analyzers disclosed herein because of that material's relatively high sensitivity and its comparatively low cost. However, lead selenide detectors are very temperature sensitive with temperature variations affecting both the bulk resistivity and the responsiveness or sensitivity of the detector material. A novel heater arrangement is therefore preferably provided to maintain the detectors at a constant and precise temperature because the errors that would be produced by variations in detector temperature cannot be eliminated simply by employing the ratioing technique discussed above. In fact, the signal from the infrared radiation detector can be lost, despite ratioing, if the detector temperature varies as little as 0.1° C.

This heating of the detectors also has the added advantage that it keeps unwanted condensation from forming on the optical components of the assembly in which the detectors are incorporated.

The novel temperature control circuitry disclosed herein is capable of controlling the detector temperature to within 0.01° to 0.001° C. In general, that circuitry receives an analog signal from a temperature sensor disposed in heat transfer relationship to the infrared radiation detectors, converts that signal to a digital form, and utilizes the digital temperature signal in a feedback loop to control the duty cycle of a strip heater. That heater is incorporated in the detector assembly and is located adjacent and in heat transfer relationship to the infrared radiation detectors.

Also, an electrical bias, typically on the order of −100 volts, is applied to the detectors of the novel gas analyzers we have invented. We have found that this appreciably increases the signal-to-noise ratio of the lead selenide detector outputs.

Another important task of the electronic circuitry preferably employed in our novel gas analyzers is to perform an auto zero function. In the circuitry we employ in our gas analyzers, both the bottom and the peak of each detector generated signal pulse are measured because a more accurate reading of the designated gas concentration can be obtained by ascertaining the actual magnitude of the pulse rather than merely its peak value. The auto zero circuitry shifts the waveform so that the bottom of the wave is always returned to a constant zero threshold before a subsequent, concentration indicative signal is generated. This insures that the waveform does not drift to an extent which might introduce errors into the concentration indicative signals.

One advantage of the novel gas analyzers just described is that they are smaller and lighter than those which have heretofore been available. As a consequence, the analyzer can be incorporated into larger patient monitoring systems in medical applications of our invention.

Also, the unit containing the infrared radiation emitter and detectors can be associated via a novel airway adapter directly into the system through which a patient's breath is exhausted rather than being disposed at a more remote location to which samples are transmitted for analysis as is commonly done in other gas analyzers. This is an advantage because distortion attributable to the transmission of the sample to the remote location is eliminated. Also eliminated are problems commonly encountered with the lines through which the sample is routed—water in the line, clogging of the line with foreign material, etc.

Another significant advantage of our novel gas analyzers is that they are much simpler than those above-discussed instruments which employ a spinning wheel or other mechanical arrangement to modulate the emitted infrared radiation. As a result, our novel instruments have a potentially lower initial cost; and they are potentially easier and less expensive to service and maintain.

Also, the power required to operate our gas analyzers is on the order of one magnitude lower than is needed to run a prior art instrument such a one employing a spinning wheel type of transducer, for example. As a result, our novel instruments can be battery powered. This is a distinct advantage as there are a number of applications—e.g., involving emergency care or otherwise requiring transportability—where a battery powered instrument is advantageous, if not required.

Yet another advantage of our novel gas analyzers over those employing spinning wheels and other moving components is that they are substantially more rugged and shock resistant.

Furthermore, our novel gas analyzers have a much faster response time than heretofore available gas analyzers operating on the non-dispersive infrared radiation absorption principle. This is important because the shape of the exhaled carbon dioxide waveform is significant in the diagnosis and treatment of many medical conditions.

Another important feature of our invention is a novel airway adapter which is employed to: (1) couple the gas analyzer into the system handling the mixture of gases being analyzed, (2) provide a path of precisely dimensioned span for the mixture of gases, and (3) provide an optical path traversing the thus confined body of gases between the infrared radiation emitter and the infrared radiation detector. This adapter can be inexpensively made of an appropriate plastic. Accordingly, it can simply be thrown away after being used. This is simpler and less expensive than cleaning and sterilizing the prior art counterpart of a heretofore available instrument as has theretofore been necessary in applications involving a human patient, for example.

In a typical application of our invention a transducer head containing infrared radiation emitting and detecting components is assembled to the disposable adapter, and the airway adapter of the resulting assembly is installed in the pathway followed by the gases being analyzed.

OBJECTS OF THE INVENTION

From the foregoing, it will be apparent to the reader that one important and primary object of the invention resides in the provision of novel, improved instruments for analyzing the concentration of one gas in a mixture of gases.

Related and also important but more specific objects of our invention reside in the provision of gas analyzers in accord with the preceding object;

which are compact, lightweight, and capable of being hand-held by a user;

which can be operated from a hand-held power supply;

which are rugged and durable in that they will continue to function properly even after being dropped onto a hard surface;

which can be used to measure any one of a wide variety of gases;

which, in conjunction with the preceding object, are particularly suited to measure the concentration of carbon dioxide in the exhalations of a medical patient.

Still another important and primary object of our invention is the provision of novel, improved transducers for generating a collimated, focused beam of infrared radiation; for screening from that beam radiation lying outside a selected, narrow band of frequencies; and for generating an electrical signal indicative of the intensity of the energy in the narrow band.

More specific but nevertheless important objects of our invention are the provision of transducers in accord with the preceding object;

which have a high signal-to-noise ratio;

which are capable of generating a beam of infrared radiation modulated at a frequency of 40–100Hz without moving parts.

Yet another important and primary object of our invention resides in the provision of novel airway adapters for confining the gases being analyzed to a path of known, precisely dimensioned span and for providing an optical path across a sample containing a gas being measured between the infrared radiation emitter and infrared radiation detector of an associated gas analyzer transaducer.

Important and related but more specific objects of the invention reside in the provision of airway adapters in accord with the preceding object:

which are inexpensive enough to be disposable in applications in which disposability is an advantage;

which are user friendly in that the associated transducer can be assembled to the airway adapter essentially without regard for orientation.

And yet another important and primary object of the present invention is the provision of a novel system for controlling the operation of a gas analyzer as characterized in the preceding objects.

Objects related to the preceding one, but more specific in nature, reside in the provision of systems as described in that object:

which are capable of maintaining the detector(s) of an infrared radiation emitting and detecting gas analyzer transducer at a constant, precise temperature;

which are capable of so applying an electrical bias to the detector(s) of an infrared emitting and detecting gas analyzer transducer as to improve the signal-to-noise ratio of the detector(s);

which are capable of comopensating for the drift in the detector(s) of an infrared emitting and detecting transducer of a gas analyzer;

which are capable of applying a pulsed voltage at a frequency of 40–100Hz to the infrared radiation emitter of a gas analyzer transducer to thereby modulate the energy emitted from said emitter.

Other important objects and features and additional advantages of our invention will be apparent to the reader from the foregoing and as the ensuing detailed description and discussion proceeds in conjunction with the accompanying drawing.

DETAILED DESCRIPTION OF THE INVENTION

The operation of the novel gas analyzer disclosed hereinbelow is controlled by a microcomputer 18 based on an Intel 8088 chip (see FIG. 9). A logic diagram for the routines run by the microcomputer is attached as Appendix A.

The microcomputer itself is not part of the present invention. For this reason and because one skilled in the relevant arts could routinely program a general purpose computer to follow the routines shown in Appendix A, the microcomputer will not be described in detail herein.

Figure 1:
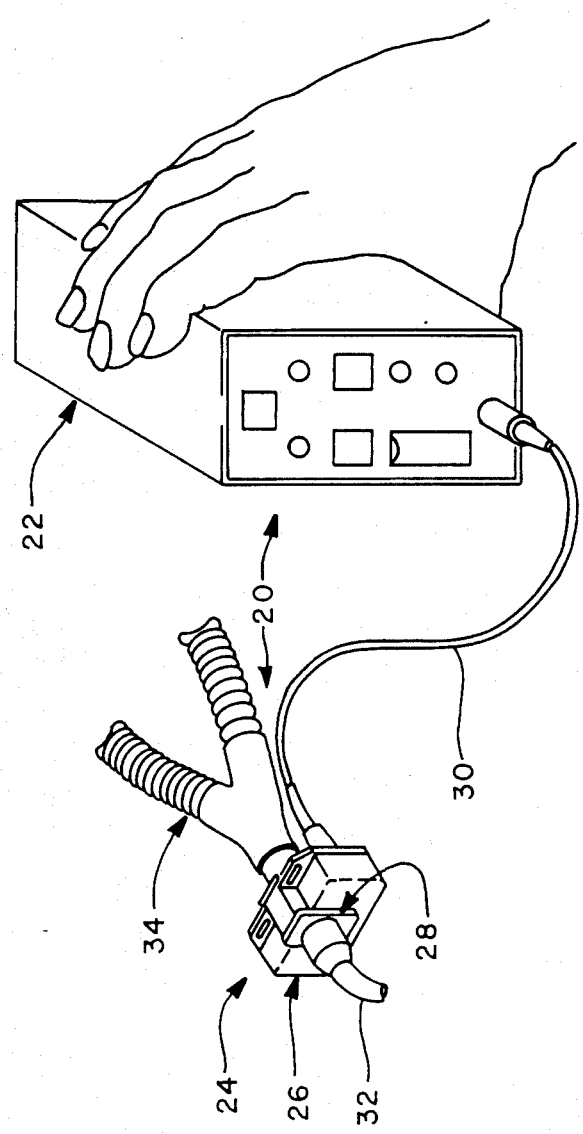
FIG. 1 is a pictorial view of a portable, hand-held gas analyzer embodying, and constructed in accord with, the principles of the present invention.

Referring now to the drawing, FIG. 1 depicts a portable, hand-held gas analyzer 20 embodying and constructed in accord with the principles of the present invention. Analyzer 20 is specifically designed to monitor the concentration of carbon dioxide in the exhalations of a medical patient—e.g., a patient being ventilated during a surgical procedure.

The major components of gas analyzer 20 are a portable, hand-held, self-powered unit 22 and an assembly 24 of a transducer head 26 and an airway adapter 28. Transducer head 26 is connected to the hand-held unit 22 of gas analyzer 20 by a conventional electrical cable 30.

In the the application of our invention depicted in FIG. 1, gas analyzer 20 is employed to measure the expired carbon dioxide level of a medical patient. This expired carbon dioxide level can be employed by medical personnel to control the operation of a mechanical ventilator hooked up to the patient to assist him in breathing. In certain major surgical procedures, the ventilator completely takes over the breathing function for the patient.

In this application of the invention, airway adapter 28 is employed to connect an endotracheal tube 32 inserted into the patient's trachea to the plumbing 34 of the mechanical ventilator (not shown). The airway adapter also confines the expired gases to a flow path 35 with a precise, transverse dimension D. The airway adapter also furnishes an optical path between an infrared radiation emitter 36 and an infrared radiation detector unit 38, both components of transducer head 26 (see FIG. 2).

The infrared radiation emitted from emitter 36 traverses the mixture of gases in airway adapter 28 where it is attenuated because part of the radiation is absorbed by the designated gas in the mixture of gases being analyzed. The attenuated beam of infrared radiation is then filtered to eliminate energy of frequencies lying outside a narrow band which is absorbed by the gas being measured. The remaining infrared radiation in that band impinges upon a detector 42 in detector unit 38. Detector 42 thereupon generates an electrical signal proportional in magnitude to the intensity of the infrared radiation impinging upon it. This signal is transmitted over cable 30 to the hand-held unit 22 of gas analyzer 20. That unit contains the microcomputer 18 and electronic circuits (see FIG. 9 and FIGS. 10–14) for controlling the operation of transducer head 26 and for converting the signal emitted by detector 42 to one indicative of the concentration of carbon dioxide in the patient's exhalations. Additional information may also be extracted from the detector-generated signal. This includes minimum inspired carbon dioxide, respiration rate, and end tidal carbon dioxide.

Figure 6:
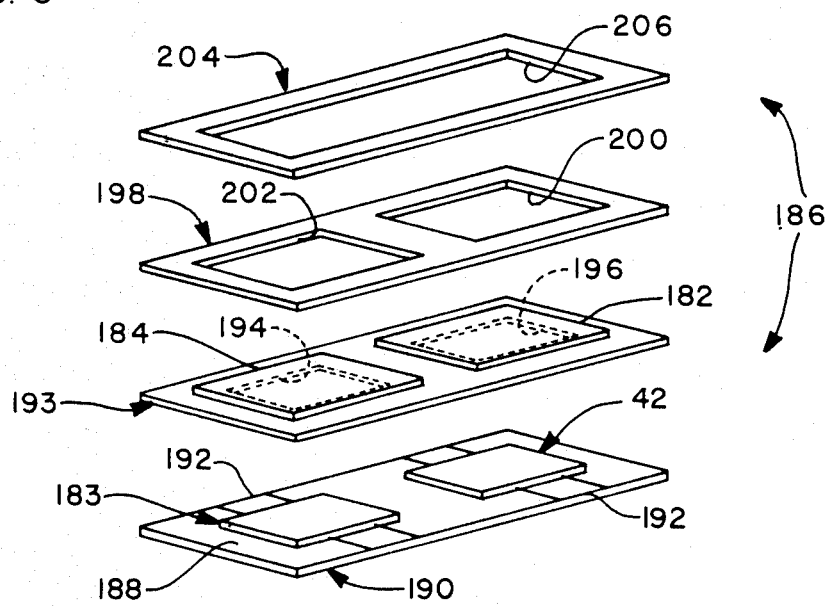
FIG. 6 is an exploded view of a filter and detector assembly incorporated in the transducer head of FIG. 3 to screen out infrared radiation which is not in a band of interest and to then produce one electrical signal indicative of the magnitude of the infrared radiation in that band and a second output signal with which the first signal can be so compared as to: (a) eliminate errors attributable to foreign material in the optical path between the infrared radiation emitter and detectors, and (b) compensate for drift in the detectors of the detector assembly.
Figure 7:
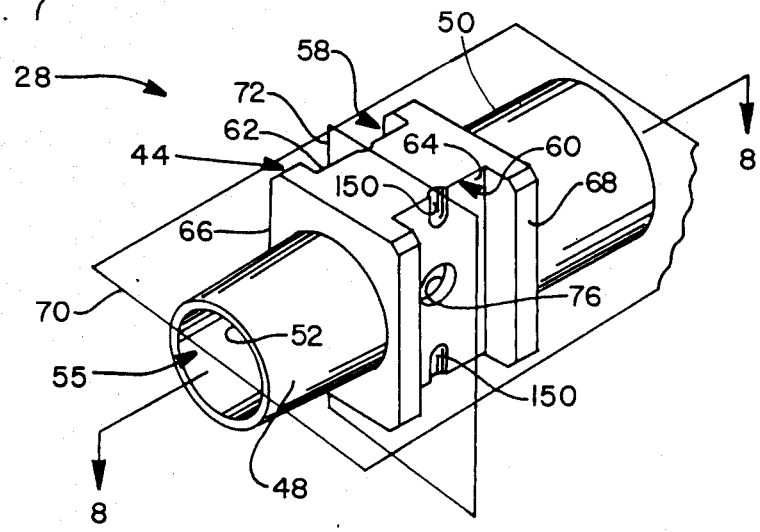
FIG. 7 is a pictorial view of an airway adapter employed in the gas analyzer of FIG. 1 to confine the gas being analyzed to a path having a precise, known, transverse dimension and to provide an optical path from the infrared radiation emitter of the transducer head shown in FIG. 2 through the mixture of gases to the detectors of the transducer head.
Figure 8:
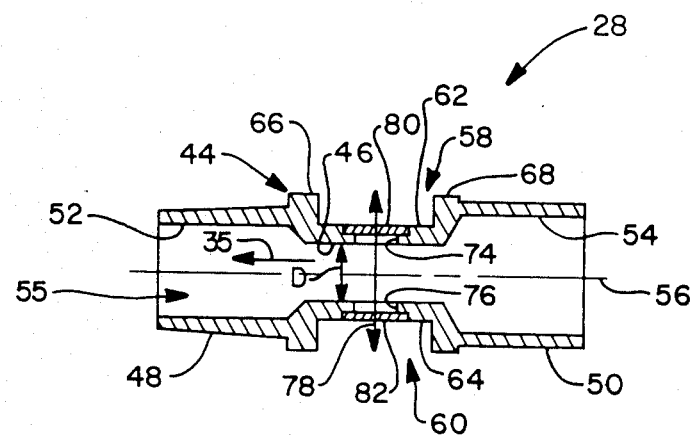
FIG. 8 is a longitudinal section through the airway adapter.

Turning now to FIGS. 6 and 7, the airway adapter 28 of the illustrated gas analyzer 20 is a one-piece unit typically molded from Valox polyester or a comparable polymer. Polymers such as Valox are preferred because they provide the ruggedness required by a suitable airway adapter. Also, airway adapters can be molded to extremely close tolerances from such polymers. This is necessary because the intensity of the infrared radiation impinging upon detector 42 is dependent upon the length of the optical path between emitter 36 and the detector, and the length of that path is controlled by the width of the airway adapter. Consequently, unless close tolerances are maintained, calibration of each individual airway adapter 28 would be required; and this might be impractical at worst and economically prohibitive at best. Furthermore, airway adapters of the illustrated configuration and fabricated from polymers such as Valox are relatively inexpensive. Consequently, they can be disposed of after being used rather than being sterilized and recycled, the conventional treatment for devices of this type.

Airway adapter 28 has a generally parallelepipedal center section 44 with a bore 46 extending from end-to-end therethrough and two hollow, cylindrical end sections 48 and 50 having through passages 52 and 54. End sections 48 and 50 are axially aligned with center section 44 along a common longitudinal centerline 56. The passages 52 and 54 in those end sections consequently cooperate with the bore 46 through center section 44 to form a single, continuous, elongated passage 55 extending from end-to-end of the aiway adapter.

Referring now to FIG. 1 as well as FIGS. 6 and 7, transducer head mounting recesses 58 and 60 are formed on opposite sides of airway adapter center section 44. These recesses furnish transducer head embraceable support surfaces at the inner ends 62 and 64 of the recesses and flanges 66 and 68 at opposite ends of the recesses. Those flanges position the assembled transducer head 26 longitudinally along the airway adapter.

As is apparent from FIG. 6, airway adapter 28 is symmetrical with respect to: (1) a longitudinally extending centerplane 70, and (2) a vertically extending centerplane 72. This is important from a practical viewpoint because transducer head 26 can consequentially be assembled to airway adapter 28 in the orientation shown in FIG. 1; or it can be turned end-for-end or upside down and still be assemblable to the airway adapter. Consequently, in addition to its other advantages discussed above, airway adapter 28 is user friendly.

As is best shown in FIG. 7, apertures 74 and 76 are formed in the center section 44 of airway adapter 28 at the inner ends or transducer embraceable surfaces 62 and 64 of receses 58 and 60. These apertures are aligned along the optical path mentioned above and identified generally by reference character 78. That optical path extends from infrared radiation emitter 36 transversely across the airway adapter and the mixture of gases flowing therethrough to the infrared radiation detector 42 in the detector unit 38 of transducer head 26. Apertures 74 and 76 are large compared to the apertures in the most comparable components of heretofore proposed gas analyzers. As a result, the novel airway adapters of the present invention are much less apt to cause errors in the concentration of the measured gas which can be attributed to dimensional variations.

To keep the gases flowing through the airway adapter 28 from escaping through apertures 74 and 76 without attenuating the infrared radiation traversing optical path 78, the apertures are sealed by sapphire windows 80 and 82. Sapphire windows are employed because other materials such as glass or plastic would absorb the infrared radiation to an extent that would significantly degrade the quality of the signal generated by detector 42. Sapphire windows are available from a variety of commercial sources. Typically, these windows will be on the order of 0.020 inch thick.

Figure 2:
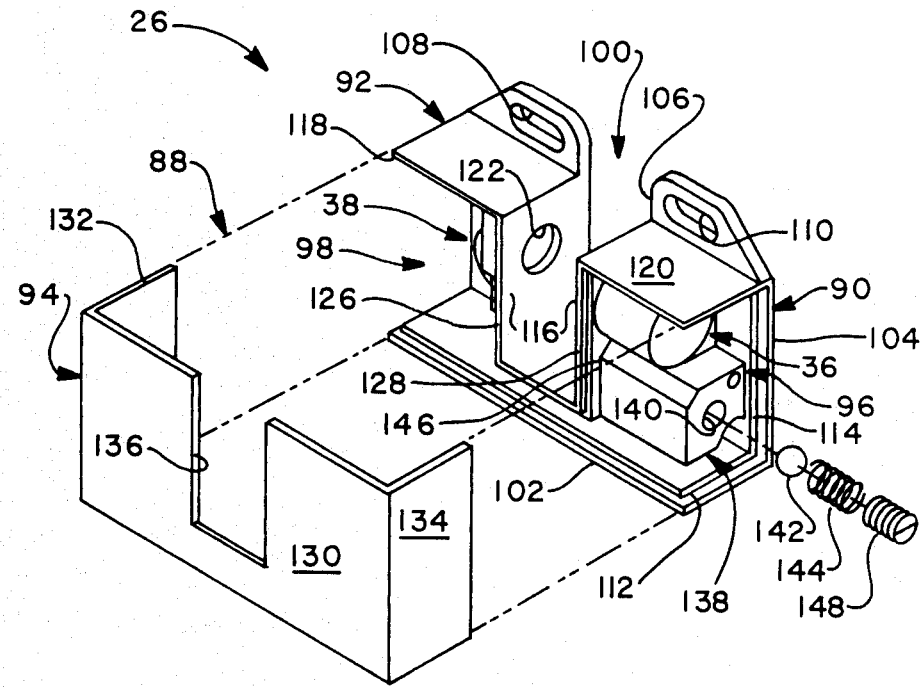
FIG. 2 is an exploded, partially pictorial view of a transducer head incorporated in the gas analyzer of FIG. 1 to generate a collimated beam of infrared radiation and to generate a signal indicative of the strength of a selected band of the infrared radiation after the beam has passed through a mixture of gases containing a gas which is of a concentration that is to be ascertained and which is capable of selectively absorbing infrared radiation in that narrow band.
Figure 3:
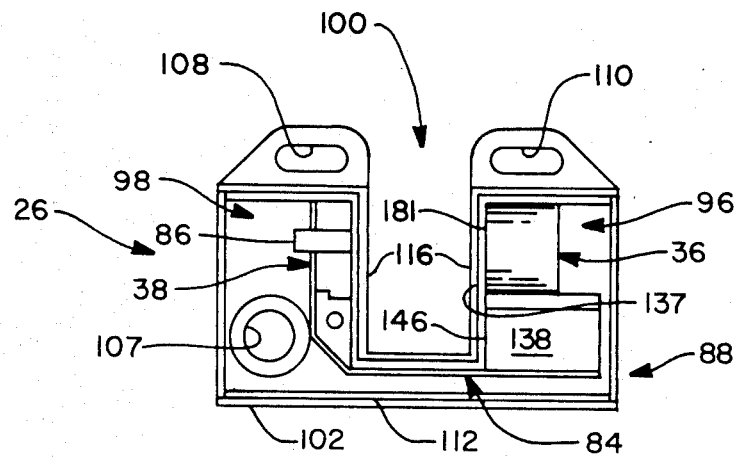
FIG. 3 is a vertical section through the transducer head of FIG. 2.

Referring now to FIGS. 2 and 3, we pointed out above that transducer head 26 includes an infrared radiation detector unit 38 which has a detector 42. Also included in the detector unit are a strip heater 84 of conventional construction and a thermistor 86 which is employed to sense the temperature of the detector unit. The thermistor and strip heater are incorporated in a system designed to keep detector unit 38 at a constant, precise temperature. As is best shown in FIG. 3, both the strip heater 84 and thermistor 86 are juxtaposed adjacent, and in intimate heat transfer relationship to, the detector 42 and the housing or casing 88 of detector unit 38.

As shown in FIG. 2, housing 88 is composed of three separate components 90, 92, and 94 which define two separate cells 96 and 98. Cell 98 houses infrared radiation detector unit 38, and cell 96 houses infrared radiation emitter 36. Located between cells 96 and 98 is a rectangularly sectioned, open top recess 100 in which the main body section 44 of airway adapter 24 is fitted (see FIG. 1).

Transducer housing component 90 has a generally L-shaped configuration provided by a horizontal base 102 and a vertically extending side wall 104. The side wall has a slot 106 therein and an aperture 107 which accommodates cable 30. Apertures 108 and 110 adjacent the upper edge of side wall 104 allow assembly 24 to be suspended from an appropriate support (not shown).

The second component 92 of transducer head housing 88 has: (1) a horizontal base 112 resting on the base 102 of housing component 90, (2) a vertical wall 114 adjacent the vertical wall 104 of component 90, and (3) a U-shaped center section 116 with top wall forming flaps 118 and 120 extending laterally therefrom.

Apertures 122 (only one of which is shown) are formed in the vertically extending side walls 126 and 128 of housing component center section 116. These apertures are aligned along the optical path 78 between infrared radiation emitter 36 and the detector 42 in infrared radiation detector unit 38.

The third component 94 of housing 88 has a vertically extending front wall 130 and vertical side walls 132 and 134. A slot or recess 136 is formed in the front wall 130 of housing component 94. This recess has the same dimensions as: (1) the recess 106 in vertically extending wall 104 of housing component 90, and (2) the gap 137 between the side walls 126 and 128 of the center section 116 of housing component 92.

Housed in cell 96 of casing 88 along with infrared radiation emitter 36 is a fitting 138 with a transversely extending passage 140 formed therethrough. Disposed in passage 140 are: (1) a spherical detent 142; (2) a spring 144, which biases detent 142 toward the inner end 146 of fitting 138; and (3) a plug 148. That plug is threaded into the through bore 140 of fitting 138 and retains the detent and detent spring in that bore. A flange (not shown) at the end of passage 140 nearest the inner end 146 of detent fitting 138 keeps detent 142 from falling out that end of the passage.

With transducer head 26 assembled to airway adapter 28 as shown in FIG. 1, for example, detent 142 is trapped in one of four complementary recesses 150 in airway center section 44 (see FIG. 7) to secure the transducer head to the airway adapter. These recesses open onto the ends of the transducer head receiving recesses 58 and 60 in the airway adapter center section 44 and thereby facilitate the separation of the transducer head 26 from the airway adapter.

Four detent trapping recesses are provided so that transducer head 26 may be coupled to airway adapter 28 in any one of the several orientations discussed above. Two of those recesses are located at the bottom 62 of transducer head receiving recess 60 and at the opposite ends of that recess. the other two detent trapping recesses are located at the bottom 64 of the second transducer head receiving recess 58 of airway adapter 28 and at the opposite ends of that recess.

Figure 4:
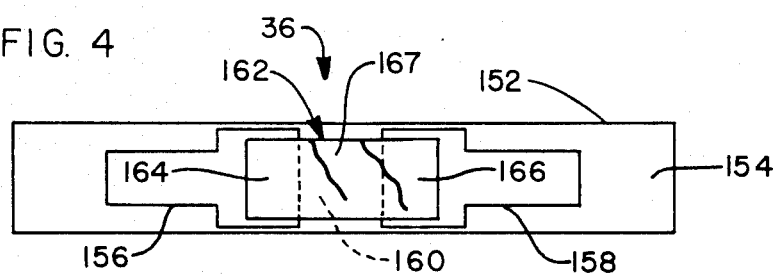
FIG. 4 is a plan view of a modulated infrared radiation emitter incorporated in the transducer head of FIG. 2.
Figure 5:
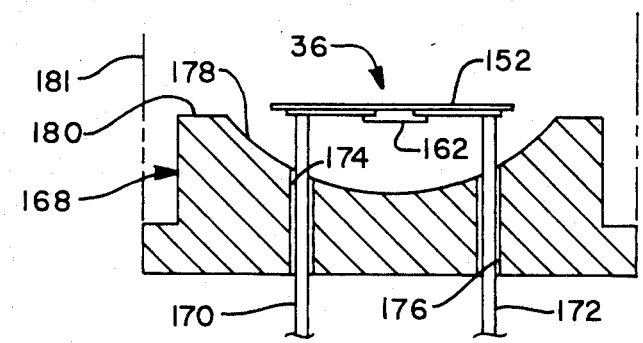
FIG. 5 is a section through an assembly which includes the radiation emitter and a support in which a mirror for collimating and focusing the emitted radiation is formed.

The infrared radiation emitter 36 housed in the just-described transducer head casing 88 is shown in more detail in FIGS. 4 and 5. Turning now to those figures, emitter 36 is of a unique thick film construction. It includes a substrate 152 which, in one actual embodiment of our invention, is 0.240 inch long, 0.040 inch wide, and 0.003 inch thick. This substrate is formed from a material having low thermal conductivity. Steatite (a polycrystaline material containing magnesium oxide and silicon dioxide) is preferred because it has a thermal conductivity which is on the order of one magnitude less than conventional low thermal conductivity materials such as alumina. This is important because it significantly reduces the power required to heat the emitter to its operating temperature.

However, alumina can be employed instead of steatite. If it is, the substrate is preferably coated with a film of a dielectric material having low thermal conductivity such as a dielectric glass.

The thickness of substrate 152 is an important parameter in the successful operation of emitter 36. To provide satisfactory performances, the emitter substrate must be in the range of 0.0025 to 0.0035 inch thick.

Figure 15:
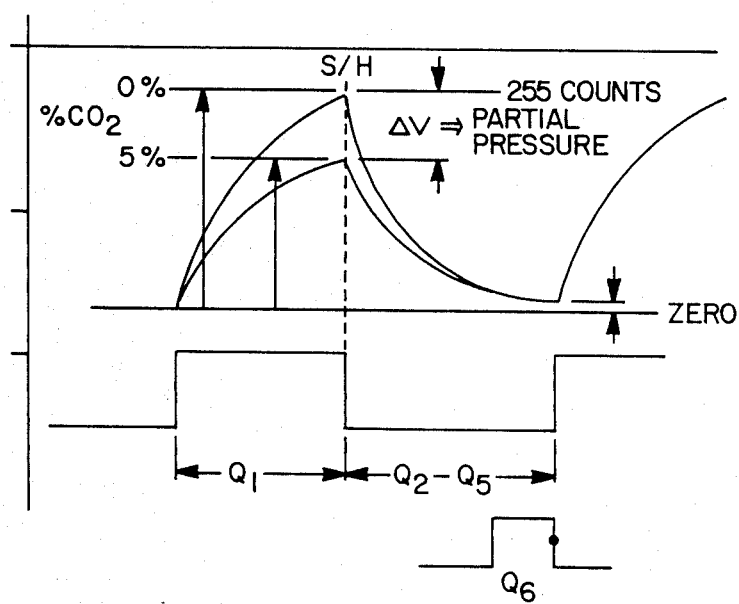
FIG. 15 is a graph showing, for two different carbon dioxide concentrations: (1) a pulse which has a typical sawtooth voltage waveform and which is indicative of measured gas concentration obtained by conversion of changing detector resistance to voltage, and (2) the segments of a detector heater duty cycle in which the heater is respectively turned on and off and a segment of that cycle in which a zero adjustment is made to compensate for shift of the pulse away from a constant zero voltage threshold.

As is apparent from FIG. 15, for an infrared emitter configuration to be of any value, a careful match between the thermal properties of the emitter's substrate and the thermal properties of the emissive material on that substrate must be made. This correlation exists in the novel, representative emitters illustrated in FIGS. 4 and 5 and discussed above and is required because the substrate and the emitter are fabricated from different materials and have quite different thermal properties as can be seen from conventional handbook data on the substrate and emitter materials we employ.

Specifically, and as is apparent from FIG. 15, the electrical detector output in a system equipped with an infrared emitter embodying the principles of our present invention has a shark's tooth waveform. This particular waveform is advantageous; and it or a comparable waveform is required because, as is also shown in FIG. 15, the result is a large change in the detector's peak output voltage for a relatively small change in the level of the carbon dioxide detected by the system. Thus, our novel systems have a high, and obviously desirable, sensitivity to variations in the concentration of the carbon dioxide being monitored. In contrast, it a less than optimum match of substrate and emitter is made—as in those previously disclosed infrared radiation emitters employing an alumina substrate and a thick film emissive element, for example—there is only a very small change in the peak detection output voltage for a comparable change in the concentration of the gas being monitored.

It is concededly possible that one might be able to obtain a useful indication of change in carbon dioxide concentration from a signal which varied to a lesser extent for a given change in carbon dioxide concentration. However, those skilled in the arts to which our invention relates will recognize that this would require much more complex and correspondingly expensive signal processing circuitry if it were possible at all. Thus, a system with an emitter as shown in FIGS. 4 and 5 and capable of generating an output with the characteristics shown in FIG. 15 has an obvious, and significant, economic advantage at the very least.

One might assume that increased modulation—perhaps comparable to that we obtain—could be obtained by increasing the input of power to the emitter. Such an assumption would, however, be incorrect because of the probability that the substrate or the emissive component, or both, would fail under the increased load.

In conjunction with the foregoing, it will be appreciated by those to whom this specification is addressed that the materials we employ as emissive elements, in the thicknesses we use, will heat up and cool very rapidly, producing sharp spikes of energy that can be reproduced in the form of electrical signals by the detectors of our novel systems. By matching the thermal characteristics of this emissive element to the thermal characteristics of the substrate to which it is mated, this spikelike waveform and the appurtenant sensitivity of our novel systems to small changes in the concentration of the gas being measured can to a large and useful extent be retained upon mating the emissive element to the matched substrate as is evident from FIG. 15.

Still another important advantage of matching the thermal characteristics of the emissive element to those of the substrate is that—as is also apparent from FIG. 15—this novel approach to infrared radiation emitter construction can be utilized to control the ratio of the energy emitted from the emissive elements of our novel infrared radiation emitters to the energy conducted away from the emissive element through the substrate. This is important because a high peak level of emitted energy is needed for sensitivity and discrimination between only slightly different concentrations in the gas being measured; and the alternative method of reaching this goal, increasing the input of power to the emitter, can cause the emitter to fail.

Bonded to the upper surface 154 of substrate 152 are two T-shaped electrical conductors 156 and 158. In the exemplary infrared radiation emitter 36 illustrated in FIGS. 4 and 5, the head of each conductor is 0.020 inch long; and the gap 160 between the conductors is 0.030 inch.

Conductors 156 and 158 are preferably formed of a platinum and gold containing cermet obtained by printing an ink such as DuPont's 4956 on the surface 154 of substrate 152 and then firing the substrate.

Superimposed on conductors 156 and 158 and bonded to the upper surface 154 of the substrate with its ends overlapping conductors 156 and 158 is a film or layer 162 of an emissive, electrically resistive material. The preferred material is obtained by firing Electro-Science Labs ESL3812 Ink. This ink has an operating temperature in the range of 250–300 degrees centigrade after it is fired.

The illustrated, exemplary, emissive layer 162 is 0.070 inch long, and the two ends 164 and 166 of the emitter overlap 0.020 inch onto the conductor 156 and the conductor 158 of emitter 36. Thus, the total overlap constitutes 57 percent of the total area of emissive layer 162. This is within the preferred and operable range of 50 to 60 percent.

Overlaps in the range just described are preferred because they tend to keep the current density at the interfaces between emissive layer 162 and conductors 156 and 158 from becoming too high and causing emitter 36 to fail by burnthrough or fatigue cracking of the emissive layer.

That we can thus prevent failures of emitter 36 is surprising. Heretofore, it has been believed that successful performance of a thick film device with an active layer-to-conductor overlap could not be obtained with an overlap exceeding about 15 percent.

Also contributing to the resistance to failure from exposure to excessive current densities is the T-shaped configuration of conductors 156 and 158. This is at least potentially superior to the more conventional rectangular or straight sided conductors as far as resistance to emissive layer burnthrough is concerned.

A film 167 of essentially pure platinum metal may be superimposed on the layer 162 of electrically resistive material to increase the emissivity of infrared radiation emitter 36. This layer of platinum is on the order of 10 to 200 Angstroms thick.

As is shown in FIG. 5, the novel infrared radiation emitter 36 just described is supported from an emitter mount 168 with the emissive element 162 facing the mount as by two emitter supporting posts 170 and 172. These posts, which extend through apertures 174 and 176 in emitter support 168, are electrically connected to conductors (not shown) in cable 30 and to the conductors 156 and 158 of infrared radiation emitter 36.

A parabolic mirror 178 is formed in the upper surface 180 of emitter support 168 facing the emissive layer 162 of infrared radiation emitter 36. This mirror collimates the infrared radiation emitted from emitter 36. It also focuses that radiation into a beam directed along the optical path 78 between the emitter and the radiation detector unit 38 of transducer head 26.

The assembly of infrared radiation emitter 36, support 168, and posts 170 and 172 is mounted in a protective can or housing 181 shown in FIG. 2 and diagrammatically in FIG. 5.

While infrared radiation emitters of the character just described can be employed to particular advantage in gas analyzers of the character disclosed in the specification, this is by no means their only use. Instead, they can be employed in virtually any application in which a modulated beam of infrared radiation of constant and known characteristics can be used to advantage.

It was pointed out above that the detector 42 on which the beam of infrared radiation impinges after traversing the mixture of gases flowing through the passage in airway adapter 28 is incorporated in detector unit 38 along with the thermistor 86 and heater 84 of the system employed to maintain detector 42 at a precise, constant temperature. Also incorporated in that unit, and ahead of the detector, in an optical filter 182. That detector unit component filters out infrared radiation of wavelengths other than one absorbed by the gas being measured.

Also preferably included in detector unit 38 are a second detector 183 and a second optical filter 184. This filter is designed to pass only infrared radiation of a wavelength that is not absorbed by the gas being measured but is adjacent the band of absorbable radiation.

As discussed above, this results in two signals being generated. The one generated by detector 42 is indicative of the concentration of the measured gas in the mixture flowing through airway adapter 28. The second detector output signal (generated by detector 183) is not attenuated by the gas being measured. As discussed above, these two signals can consequently be ratioed to eliminate significant errors in the measured concentration of the designated gas. These errors are attributable to such factors as foreign substances in opitcal path 78 (for example, condensation on airway adapter windows 80 or 82) and drift or other minor, uncompensated for, instabilities in detectors 42 and 183.

The just-described assembly of detectors 42 and 183 and optical filters 182 and 184 is illustrated in FIG. 6 and identified by reference character 186.

In this assembly, detectors 42 and 183 are mounted in spaced apart relationship on the surface 188 of a substrate 190.

Detectors 42 and 183 are preferably made from lead selenide because of the sensitivity to infrared radiation which that material has.

Figure 9:
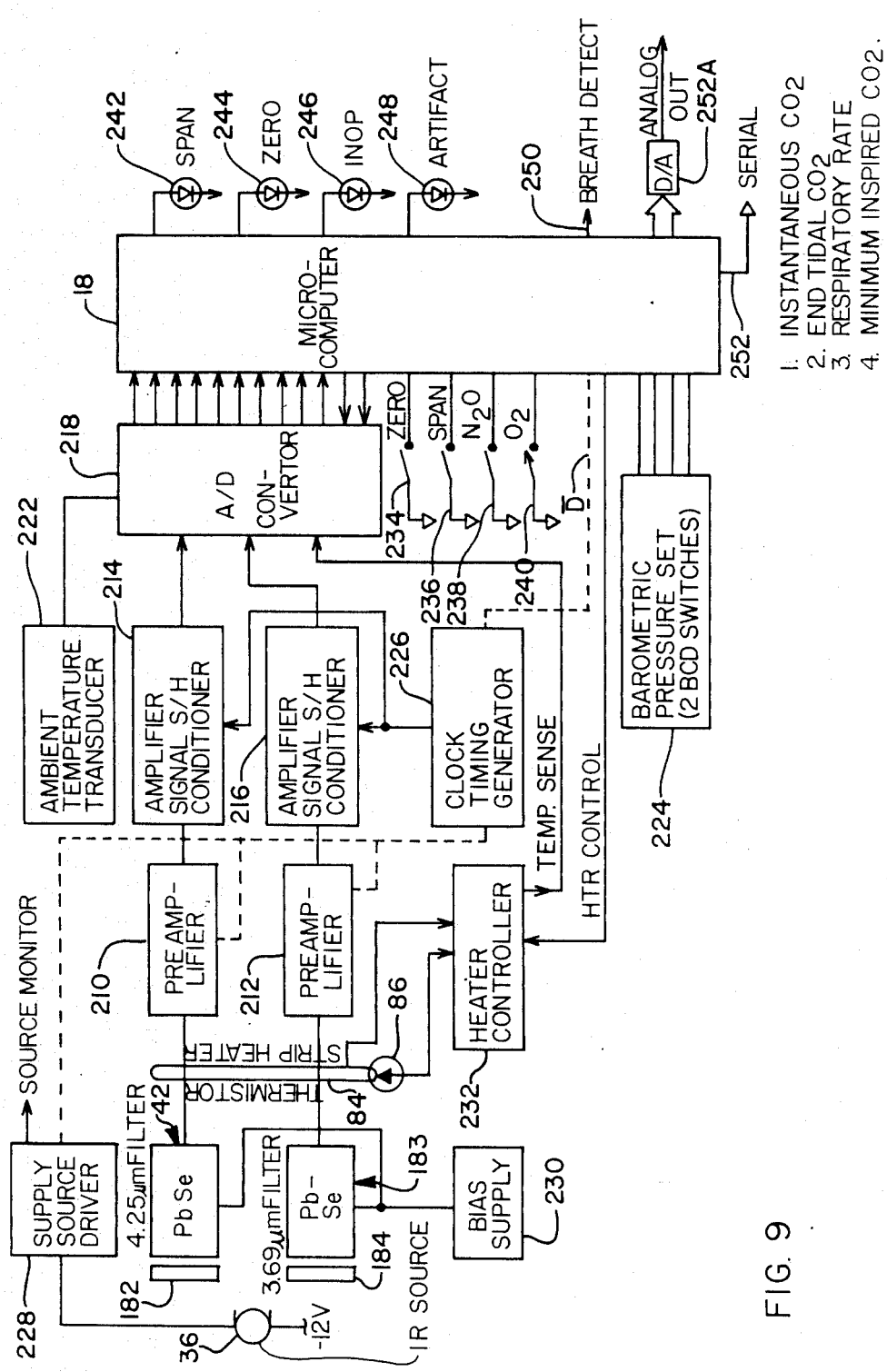
FIG. 9 is a block diagram of the gas analyzer of FIG. 1.

Leads 192 illustrated schematically in FIG. 6 connect detectors 42 and 183 to the signal processing system of gas analyzer 20 (see FIG. 9).

Also mounted on the base or substrate 190 of assembly 186 is a filter support 193. Formed in that support are apertures 194 and 196 corresponding in location and configuration to detectors 42 and 183. Apertures 194 and 196 provide an interference free path through filter support 193 for the infrared radiation beamed along optical path 78 from emitter 36.

Mounted on filter support 193 and spanning apertures 194 and 196 are the above-discussed optical filters 182 and 184. Those filters are conventional and commercially available and will accordingly not be described in detail herein.

In the illustrated, exemplary embodiment of our invention (designed to measure the concentration of carbon dioxide in a mixture of gases), filter 182 is preferably designed to pass to detector 42 only infrared radiation in a narrow band (typically 150 angstroms wide) centered on a frequency of 4.25 microns. Filter 184, on the other hand, is designed to transmit to detector 183 only infrared radiation in a similarly narrow band centered on an adjacent frequency of 3.69 microns. That energy is not absorbed by carbon dioxide.

Filter support 193 also supports a protective filter frame 198. This frame has two apertures 200 and 202. Filters 182 and 184 are fitted in these apertures and surrounded by the end and edge portions of the protective frame.

Finally, the assembly 186 shown in FIG. 6 includes a top cover 204. An aperture 206 in the top cover allows the infrared radiation beamed from infrared radiation emitter 36 along path 78 to reach filters 182 and 184 in assembly 186 without interference from, or attenuation by, that cover.

The base or substrate 190 of assembly 186, filter support 193, and filter frame 198 are preferably fabricated of a material having moderate thermal conductivity such as alumina because it is necessary for the assembly to attain and maintain a constant temperature within a reasonable time at a low power input level. Top cover 204 is fabricated of a polymer such as Kovar because that material has the same expansion coefficient as alumina.

Turning next to FIG. 9, the electrical signals generated by the lead selenide infrared radiation detectors 42 and 183 in the just-described detector unit 38 are transmitted to synchronous preamplifiers 210 and 212. It is the function of these preamplifiers to amplify the electrical signals generated by the lead selenide infrared radiation detectors.

The output signals from preamplifiers 210 and 212 are routed to essentially identical signal conditioning systems 214 and 216. In these systems, the amplified, detector-generated signals are conditioned and then subjected to a sample-and-hold process. In this respect, and as was discussed above and is shown in FIG. 15, the signals generated by detectors 42 and 183 typically have a sawtooth waveform. The sample-and-hold technique is employed to detect the voltage at the peak of each wave. This is done in order to measure the partial pressure of the designated gas as a function of peak signal amplitude. The sample-and-hold circuit output is routed through a conventional multiplexer (not shown) in an analog-to-digital convertor 218 to sequentially convert the signals one at a time. The multiplexed signal is digitized to generate an appropriate digital input for microcomputer 18.

The major functions of the microcomputer 18 of gas analyzer 20 are: (1) to control the temperature of the infrared radiation detectors 42 and 183, (2) to control the modulation of infrared radiation emitter 36, and (3) to convert the information on the concentration of the designated gas transmitted to it from analog-to-digital convertor 218 into a form in which that information can be readily utilized by the user of gas analyzer 20.

As pointed out above, the routines followed by microcomputer 18 in carrying out these tasks appear in Appendix A.

Also routed to analog-to-digital convertor 218 is a signal generated by an off-the-shelf, commercially available, ambient temperature transducer 222. This transducer signal is used to compensate for the effect which the temperature of the gases flowing through airway adapter 28 has on the absorption of the infrared radiation impinging upon detector 42. Changes in the output signal from that detector which are attributable to temperature changes rather than changes in the concentration of the designated gas are thereby eliminated.

The novel gas analyzer 20 disclosed herein also includes a provision for factoring local barometric pressure into the algorithms solved in microcomputer 18 to convert the output signal from detector 42 to a display indicative of the concentration of the designated gas in that mixture of gases flowing through airway adapter 28. This is important because the detector output signal is dependent upon barometric pressure as well as the concentration of the designated gas.

In the illustrated embodiment of the invention, the barometric pressure factor is supplied by way of a unit 224 consisting primarily of two binary coded decimal switches (not shown). The details of these switches and their input connections to microcomputer 18 are conventional and not part of the present invention. They will, accordingly, not be described herein.

Another major component of the system illustrated in FIG. 9 is a clock timing generator 226. The clock timing generator so turns on and off the synchronous amplifiers 210 and 212 that the output signals from the latter are in a pulsed as opposed to continuous form. These pulses, which represent partial pressure, are inputted to microcomputer 18 rather than continuous detector originated signals because microcomputer 18 operates as a sample data system.

Clock timing generator 226 is also connected to a supply source driver 228. That component alternately turns radiation emitter 36 on and off to modulate the emission of infrared radiation from emitter 36 at the preferred frequency of 40-100 Hz.

Yet another major component of gas analyzer 20 shown in FIG. 9 is a bias supply 230. This unit is employed to apply the above-discussed electrical bias to lead selenide detectors 42 and 183 and thereby improve the signal-to-noise ratios of those detectors.

The last of the major system components shown in FIG. 9 is a heater controller 232. The input to the heater controller is the temperature indicative signal generated by the thermistor 86 juxtaposed to the substrate 190 of infrared radiation detector assembly 186. This temperature indicative signal is processed in the heater controller and transmitted to analog-to-digital convertor 218. Here, this signal is also multiplexed and converted to a digital format which can be inputted to microcomputer 18. As discussed above, the microcomputer thereupon computes that portion of the duty cycle for which the strip heater 84 of detector unit 38 needs to be turned on to keep detectors 42 and 183 at the wanted temperature. This duty cycle information is transmitted back to, and controls the operation of, the heater controller 232.

Referring still to FIG. 9, microcomputer 220 also has four inputs 234, 236, 238, and 240 identified as ZERO, SPAN, N₂O, and O₂. These four inputs are all user-selected and initiated.

The N₂O and O₂ inputs 238–240 are utilized to compensate for nitrogen oxides and/or oxygen in the mixture of gases being analyzed in applciations of our invention such as the medical application under discussion. These compensations are employed in instances in which appreciable amounts of oxygen and/or nitrogen oxides are present in the mixture because both nitrogen oxides and oxygen affect the infrared radiation absorption of carbon dioxide even though they do not absorb infrared radiation of the 4.25 micron wavelength reaching detector 42. Absent correction for oxygen and/or nitrogen oxides, therefore, the detector might report a concentration of carbon dioxide which is erroneous to a significant extent.

The ZERO input 234 is likewise employed to introduce a compensation factor into the concentration of the measured gas calculated by microcomputer 18 in applications such as those discussed above in which the concentration of carbon dioxide in a medical patient's exhalations is being measured. The air present in an enclosed space, for example a hospital room, typically contains approximately 0.03 percent carbon dioxide. The ZERO input instructs microcomputer 18 to subtract this amount from the calculated concentration of carbon dioxide so that the numerical concentration displayed to the user will more accurately reflect the patient's medical condition.

Finally, SPAN input 236 is employed in applications of gas analyzer 20 in which that instrument is utilized to measure the concentration of a designated gas in a mixture of gases which is contained in a closed cell rather than the concentration of a designated gas in a dynamic system such as the one illustrated in FIG. 1. In the static situation, the SPAN input is employed to input to microcomputer 18 the known volume of the sealed cell containing the mixture of gases being analyzed.

Microcomputer 18 also has four status indicating displays 242, 244, 246, and 248. SPAN and ZERO displays 242 and 244 are lit when SPAN and ZERO compensations are employed.

An INOPERATIVE display 246 is illuminated when a mechanical malfunction, for example of heater controller 232, occurs.

Finally, ARTIFACT display 248 is illuminated when microcomputer 18 is unable to interpret the information inputted to the microcomputer from analog-to-digital convertor 218 in a meaningful manner. This typically happens when there is a significant abberation in the configuration of the waveform reflecting the concentration of the gas being measured. In this event, the illumination of ARTIFACT display 248 indicates to the user of gas analyzer 20 that there are errors in the data being received by the microcomputer.

In the medical applications of our invention for which gas analyzer 20 is particularly designed, microcomputer 18 also has a number of outputs. One of these is identified by reference character 250 and the label BREATH DETECT. This output is enabled each time gas analyzer 20 detects a breath, whether or not mechanically assisted, by the medical patient being monitored.

A second output is designated by reference character 252 and labelled SERIAL. This output is employed to supply a variety of information including the instantaneous concentration of the designated gas being measured. That information is continuously updated during the part of each operating cycle of emitter 36 in which the emitter is turned on.

A second type of information that can be supplied at serial output 252 is end tidal carbon dioxide. This is the peak value of the carbon dioxide concentration in each exhalation of the patient being monitored.

In addition, microcomputer 18 can supply the patient's respiration rate and the minimum concentration of inspired carbon dioxide, both by analysis of the sawtooth waveform shown in FIG. 15.

As shown in FIG. 9, microcomputer 18 also has the ability to convert the INSTANTANEOUS digital output to an analog form by way of a parallel output connected to a digital-to-analog convertor 252A. An analog output is useful because it can be recorded by a chart recorder for example. This recorder provides the user with a hard copy record for the patient's medical chart.

The signal conditioners 214 and 216 employed to process the amplified pulses generated in preamplifiers 210 and 212 from the detector 42 and 183 output signals are significant components of the system illustrated in FIG. 9. The two amplifier units are essentially identical. The one of these identified by reference character 214 is depicted in more detail in FIG. 10 along with the associated preamplifier 210 and the bias supply 230 employed to increase the signal-to-noise ratio of detector 42. Only this signal conditioner will be described herein. It is to be understood by the reader that this description is equally applicable to signal conditioner 216 and its associated preamplifier and the bias supply for detector 183.

The bias supply is typically a minus 100 volts. The bias is applied to detector 42 through a resistor R253 which is employed to convert the bias voltage to a corresponding bias current.

Figure 10:
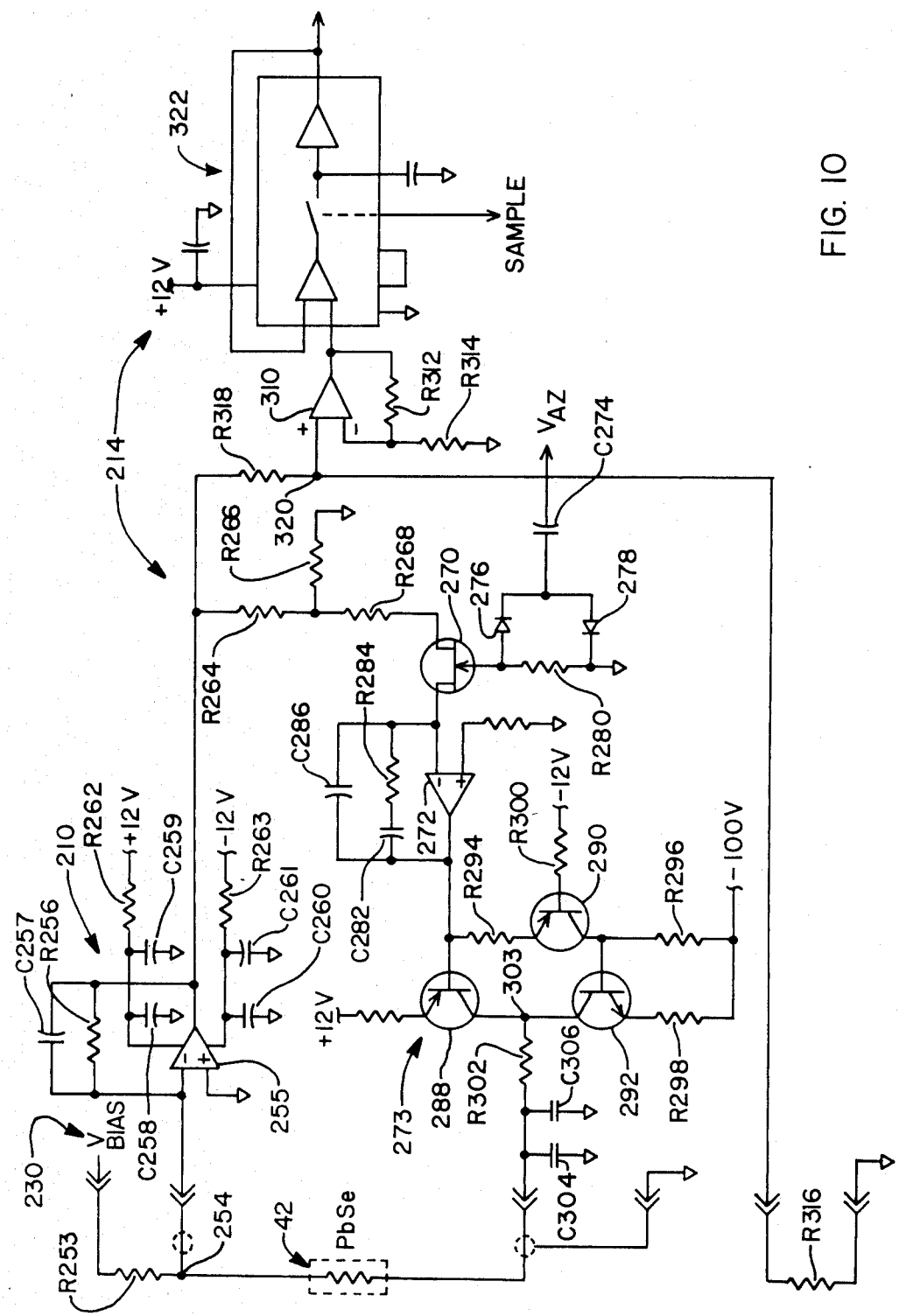
FIG. 10 is a schematic diagram of one of two essentially identical systems utilized in the gas analyzer of FIG. 1 to process the signals generated by the infrared radiation detectors in the transducer head of FIG. 2.

As is apparent from FIG. 10, resistor R253 is physically incorporated in transducer unit 38 in series with detector 42 rather than in hand-held unit 22 with the remainder of the electronic circuitry. By selecting a resistor R253 of the appropriate resistance, variations in the lead selenide detectors can be compensated for so that the performance characteristics of each detector unit 38 will be the same. The incorporation of resistor R253 in the detector unit therefore allows a transducer head 26 to be replaced in the field without recalibration of the gas analyzer electronics.

An electrical signal is generated by detector 42 when the gas being measured is present in the mixture of gases being analyzed. This signal is summed with a bias voltage $V_{BIAS}$ at a summing junction 254, and the resultant signal is applied to the inverting input of an operational amplifier 255 which is connected to operate as a high gain amplifier in order to boost the signal by a factor of approximately 100. A feedback circuit consisting of a resistor R256 and a compensating capacitor C257 is connected between the output of operational amplifier 255 and its inverting input to control the amplifier gain.

Operational amplifier 255 is powered from both plus 12 volt and minus 12 volt power supplies. Bypass capacitors C258, C259, C260, and C261 and resistors R262 and R263 are connected between the power supplies and the operational amplifier 255 to provide noise filtering. This is necessary because the input signal to operational amplifier 255 very small and because the amplifier has a very high gain. Consequently, unless noise is eliminated or minimized, the input signal can easily be lost.

The output signal from operational amplifier 255 is applied to a voltage divider network consisting of resistors R264 and R266 and having an approximately 10:1 ratio and then through a dropping resistor R268 to a series source, drain-connected, field effect transistor 270. When turned on, transistor 270 applies a voltage to the inverting input of an operational amplifier 272. That amplifier is employed to drive the high voltage, transistor-based amplifier stage or current convertor 273 described below.

Field effect transistor 270 is turned on by applying a control voltage to its gate. This control voltage, designated $V_{AZ}$ in FIG. 10, is varied as necessary by microcomputer 18 in a manner discussed below. The adjustment compensates for the above-discussed drift of detector 42 from the threshold level as shown in FIG. 15.

The control or auto zero voltage $V_{AZ}$ is applied through a capacitor C274 to the anode of a diode 276 and the cathode of a diode 278. Diode 276 is connected to the gate of field effect transistor 270, diode 278 is connected to ground, and a biasing resistor R280 is connected to ground in parallel with diode 278.

The purpose of the circuit containing diodes 276 and 278 and resistor R280 is to reference $V_{AZ}$ signal to ground. This accomplished by the repetitive $V_{AZ}$ signal charging capacitor C274 through diode 278.

The internal operation of operational amplifier 272 is controlled by a feedback network. That network consists of a serially connected capacitor C282 and resistor R284 and a second capacitor C286 connected across the serially connected capacitor and resistor. Capacitor C282 is the primary feedback control component. The serially connected resistor R284 and the parallel connected capacitor C286 constitute a network which provides control loop compensation.

This voltage output signal from operational amplifier 272 is converted to the above-mentioned current signal in above-mentioned current convertor 273. That circuit consists of transistors 288, 290, and 292 and resistors R294, R296, R298, and R300. This current convertor is a conventional one. Its function is to provide a zero adjusting current equalling the bias current flowing to detector 42 through resistor R253. With the biasing current and zero adjusting current equal, the signal applied to the inverting terminal of operational amplifier 255 is accurately indicative of the concentration of the measured gas as detected by detector 42.

A resistor R302 is connected between detector 42 and a junction 303 between transistors 288 and 292 in the zero adjust circuit just described to provide a fixed A.C. impedance. A pair of capacitors C304 and C306 are provided to provide a low A.C. impedance.

It was pointed out above with respect to the circuitry shown in FIG. 9 that both the operation of the preamplifier 210 just described and the supply source driver 228 which turns infrared radiation emitter 36 on and off are controlled by clock timing generator 226. In particular, the preamplifier and supply source driver are so regulated by the clock timing generator that the zero adjust current just described is applied to lead selenide detector 42 at the end of the off segment of the on-off cycle of infrared radiation emitter 36. This mode of operation is selected because the times when the zero sample-and-peak samples are taken are adjacent to each other.

Referring still to FIG. 10, the concentration indicative output signal from operational amplifier 255 is also transmitted from the divider network consisting of resistors R264 and R266 to the non-inverting terminal of an operational amplifier 310. Operational amplifier 310 has a 20:1 gain controlled by a feedback resistor R312.

The inverting terminal of operational amplifier 310 is connected through a resistor R314 to ground. This resistor provides a ground reference.

Also connected to the non-inverting terminal of operational amplifier 310 is a factory-selected gain adjust resistor R316. The responsivity of lead selenide varies from detector to detector. Each resistor R316 is matched to the detector with which it is to be associated so that the response of each detector will be the same. Again, that eliminates the calibration of gas analyzer 20 that would otherwise be required each time a transducer head 26 is replaced.

The just-described gain adjust resistor R316 and a resistor R318 located between operational amplifiers 255 and 310 together constitute an attenuator which has a maximum attenuation of not more than 2:1. As a result, maximum attenuation occurs when there is no current flow at the junction 320 between resistors R316 and R318. This just-described attenuator is provided to provide gain adjustment as required by each different detector 42.

The output signal from operational amplifier 310 is applied to the input of a sample-and-hold circuit 322 which is provided to sample the peak or the zero signal. This circuit is conventional and will accordingly not be described herein. It is, however, a significant feature of our invention as it keeps the voltage across analog-to-digital convertor 218 constant while analog-to-digital conversions are being made at a level representing the analog input as of a precisely known time.

Circuit 322 is designed to sample the signal transmitted to it from operational amplifier 310 periodically, typically at intervals on the order of 2 milliseconds, while infrared radiation emitter 36 is turned on. Also, the output from operational amplifier 310 can be sampled after the infrared emitter 36 has been off for a specified time. This produces a signal which is indicative of the zero value of the signal generated by lead selenide detector 42. Consequently, the just-mentioned signal is one which can be employed by microcomputer 18 to perform the zero adjustment discussed above.

The analog output signal from sample-and-hold circuit 322 is routed to the multiplexer in analog-to-digital convertor 218 where the data and reference signals and zeros are sequentially switched to the circuitry which performs the analog-to-digital conversion. The multiplexer output is converted to a digital input for microcomputer 18, enabling the latter to furnish the displays and perform the control functions discussed above.

We pointed out above that clock timing generator 226 is incorporated in the electrical circuitry of gas analyzer 20 to turn infrared radiation emitter 36 on and off and to provide detector generated pulses which can be sampled, either: (1) during that part of the duty cycle in which the infrared radiation emitter 36 is turned on, or (2) during that part of the cycle and also during the off part of the duty cycle to provide zero pulses for adjustment purposes.

Figure 11:
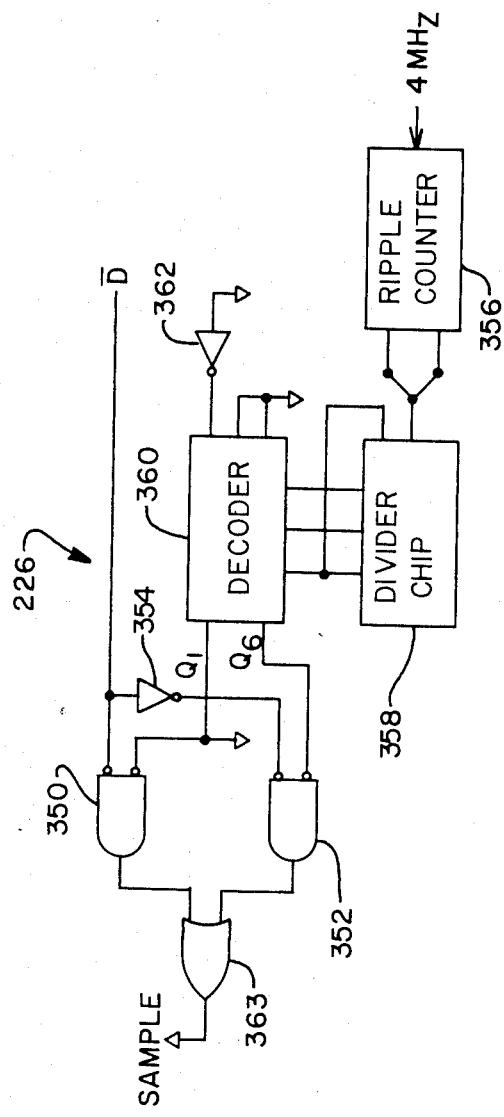
FIG. 11 is a schematic diagram of a clock timing generator employed to control the operation of the system shown in FIG. 10 and the modulation of the infrared radiation emitter of FIG. 5.

This clock timing generator, illustrated in more detail in FIG. 11, emits timing signals at a rate selected by microcomputer 18. The microcomputer output, $\overline{D}$, is applied to, and controls the operation of, two AND gates 350 and 352. The $\overline{D}$ signal is applied to the latter gate, 352, through an inverter 354 to cause the sampleand-hold circuit 322 to select either gas concentration data or zero information on command.

Timing clock generator 226 also includes: (1) a conventional 14-stage ripple counter 356 which is supplied with a 4 mHz drive signal and a divide-by-six programmable divider chip 358 with a triple input to a conventional decoder 360 connected through an inverter 362 to ground. This inverter is provided to provide a logic one to decoder 360.

The 4 mHz signal is reduced by ripple counter 356 to either a 480 Hz or a 240 Hz output signal. This output signal is routed to a clock (not shown) in chip 358 which consequentially generates an output having the six segments identified as $Q_1$ through $Q_6$ in FIG. 15 during each on-off or duty cycle of infrared radiation emitter 36.

$Q_1$ is the segment representing the infrared radiation emitter "on" time. During this portion of the duty cycle, the output from decoder 360 enables AND gate 350. This result in a signal which is routed to an OR gate 363. This causes gate 363 to output the signal labelled SAMPLE in FIG. 11. The SAMPLE signal enables supply source driver 228 which accordingly turns on infrared radiation emitter 36 for that part of the duty cycle computed by microcomputer 18.

The SAMPLE signal also enables synchronous preamplifiers 210 and 212, allowing the signals generated by lead selenide detectors 42 and 183 to be processed and transmitted to microcomputer 18 in the manner discussed above to furnish the displays and provide the controls for which the microcomputer is designed.

$Q_2$ through $Q_5$ represent that part of the duty cycle in which the infrared radiation emitter 36 is turned off. This is accomplished by removing the enabling signal from AND gate 350 at the end of the on segment $Q_1$ in each duty cycle of radiation emitter 36. When this occurs, OR gate 363 shuts off. Therefore, it ceases to supply the SAMPLE signal needed to operate supply source driver 228 and to permit preamplifiers 210 and 212 to route zero pulses generated in those preamplifiers from the infrared radiation detector output signal to the signal processing circuitry depicted in FIG. 10.

Finally, $Q_6$ is that segment of the duty cycle of infrared radiation emitter 36 in which the zero adjust function discussed above is performed. In that segment of the duty cycle, AND gate 352 is enabled by decoder 360. This enables OR gate 363, thereby routing the zero adjust input signal $V_{AZ}$ discussed above to signal conditioner 214 to compensate for drift of lead selenide detector 42.

Figure 12:
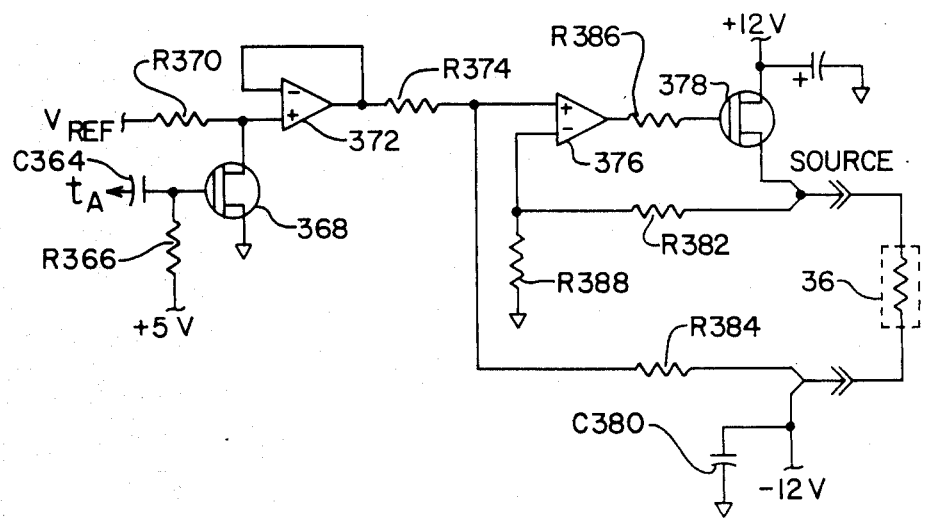
FIG. 12 is a schematic diagram of a supply source driver employed to apply electrical pulses to the infrared radiation emitter of FIG. 5 at a frequency of 40–100Hz.

Referring still to the drawing, FIG. 12 illustrates, in detail, the supply source driver 228 which is activated during that segment of the infrared radiation emitter duty cycle designated $Q_1$ in FIG. 15 to turn on infrared radiation emitter 36. This signal is applied through a capacitor C364 and resistor R366 to the gate of a field effect transistor 368. This transistor is also connected across a reference voltage source through a resistor R370 which isolates the reference voltage ($V_{REF}$) from ground when field effect transistor 368 is turned on. Therefore, during the $Q_1$, emitter on segment of the infrared radiation emitter duty cycle, field effect transistor 368 is turned off.

Field effect transistor 368 insures that the circuit connecting infrared radiation emitter 36 to its sources of operating voltage is, or remains, interrupted if clock timing generator 226 fails. Absent the protection circuit, the infrared radiation emitter would remain continuously on and would fail almost immediately, requiring that transducer head 26 be replaced.

The turning on of field effect transistor 368 removes the reference voltage signal from the non-inverting terminal of an operational amplifier 372. Removal of this control voltage turns on amplifier 372 which has its output connected to its inverting input so that it functions as a unity follower. A unity follower is needed at this point in the supply source driver to buffer the reference voltage.

The output from operational amplifier 372 is connected through a resistor R374, which sets the amplifier gain, to the non-inverting terminal of a second operational amplifier 376 in supply source driver 228. That operational amplifier is one component of a differentially connected amplifier-and-follower combination which also includes field effect transistor 378. This amplifier-and-follower combination is employed to provide gain and a 150 milliampere output current drive capability.

The source of field effect transistor 378 is connected to one end of infrared radiation emitter 36, and the opposite end of the emitter is connected to a minus 12 volt power source having a capacitor C380 connected in parallel therewith to provide local power supply filtering. Consequently, when field effect transistor 378 is partially or fully turned on, infrared radiation emitter 36 is connected across the plus 12 and minus 12 volt power supplies; and current flows through it, causing infrared radiation of the wanted, controlled characer to be emitted.

The magnitude of the power applied to infrared radiation emitter 36 is crucial because variations will affect the magnitude of: (1) the radiation emitted in the 4.25 micron-centered band impinging upon detector 42, and (2) the energy emitted in the 3.79 micron-centered band impinging upon detector 183. Therefore, variations in the power supplied to emitter 36 would cause those detectors to report changes in the concentration of the designated gas which are attributable to variations in that power rather than to changes in the concentration of the measured gas as both detectors are involved in the generation of the ratioed, error compensated, gas concentration signal.

Unwanted irregularities of the character just described are eliminated by employing a differential resistor network to provide a precise, constant power source for emitter 36. This network includes: (1) a resistor R382 connected between the inverting terminal of operational amplifier 376 and infrared radiation emitter 36, (2) a resistor R384 connected between the non-inverting input of operational amplifier 376 and ground through the above-discussed capacitor C380, (3) a resistor R386 connected between operational amplifier 376 and the source of field effect transistor 378, and (4) a resistor R388 connected between the inverting input of operational amplifier 376 and ground. Resistors R388 and R370 are matched as are resistors R382 and R384. Therefore, the voltage applied across infrared radiation emitter 36 is precisely related to the reference voltage; and the infrared radiation detector is turned on and off in an essentially instantaneous fashion; i.e., the voltage applied across emitter 36 follows an essentially square waveform.

Figure 13:
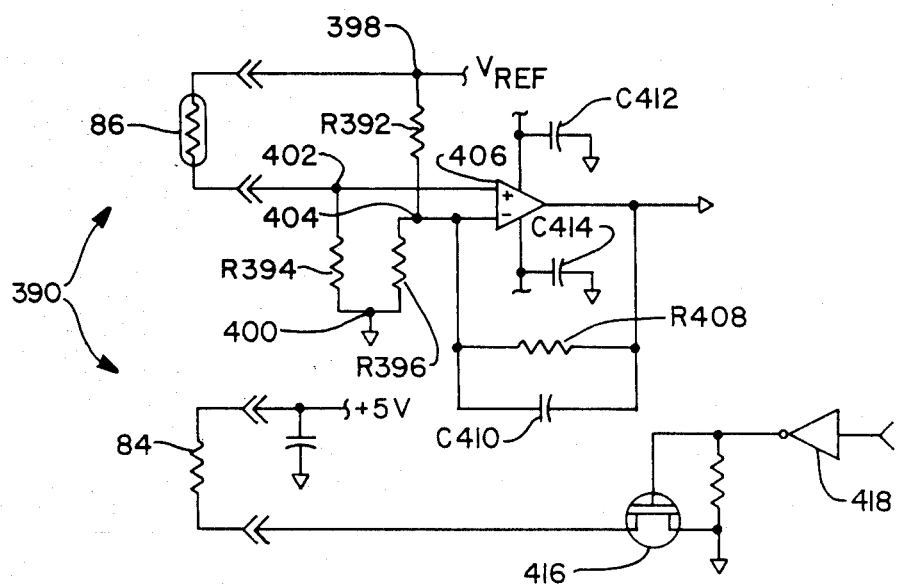
FIG. 13 is a schematic of a circuit employed in the gas analyzer of FIG. 1 to control the temperature of the infrared radiation detectors.

In the system depicted in FIG. 13, a constant voltage source is employed to operate emitter 36 rather than a constant power source. A constant voltage source is inherently more stable, and stability is a prerequisite to accuracy in gas analyzers operating on the principles disclosed herein.

Furthermore, a bipolar power supply, typically plus and minus 12 volts, is preferably employed rather than the more common single-sided power supply. This makes it possible to power gas analyzer 20 with a battery, thereby making that instrument self-contained.

We also pointed out above that lead selenide is extremely temperature sensitive and that, as a consequence, successful operation of gas analyzer 20 requires that infrared radiation detectors 42 and 183 be precisely maintained at a constant temperature. The system by which this control function is accomplished includes the above-discussed strip heater 84 and thermistor 86, and it is identified in FIG. 13 by reference character 390.

Thermistor 86 is located in one leg of a bridge which also includes resistors R392, R394, and R396. Reference voltage $V_{REF}$ is applied to one reference terminal 398 of the bridge, and the second reference terminal 400 is connected to ground. The two output terminals 402 and 404 of the bridge are respectively connected to the non-inverting and inverting inputs of an operational amplifier 406 with terminal 402 also being connected through biasing resistor R394 to ground. Therefore, operational amplifier 406 is turned on when the detector unit temperature sensed by thermistor 86 departs from the reference temperature because: the resistance of thermistor 86 changes, the just-discussed bridge becomes unbalanced, and current thereby flows in the bridge circuit.

Connected across the output and the inverting input of operational amplifier 406 is a low-pass filter consisting of a resistor R408 and a capacitor C410. This filter eliminates those frequencies of the signals applied to operational amplifier 406 which, because of the characteristics of a thermistor, are not representative of changes in the thermistor-sensed temperature.

Also connected to operatinal amplifier 406 are capacitors C412 and C414. These capacitors provide local power supply filtering.

Because feedback resistor R408 and bridge resistors R392, R394, and R396 cooperate with thermistor 86 to perform a temperature-to-voltage conversion, the output from operational amplifier 406 is a detector temperature-proportional voltage. This voltage varies from zero volts at a detector temperature of 35° C. to plus 5 volts at a detector temperature of 45° C. This operational amplifier output signal is routed to the multiplexer is analog-to-digital convertor 218 to allow for sequential signal conversion. The multiplexer output signal is converted to a digitized signal and routed to microcomputer 18.

The digitized information is compared in microcomputer 18 to the operating temperature selected for detector unit 38 through an algorithm encoded in the microcomputer. The result is a computed duty cycle with the time segment $Q_1$ (see FIG. 15) representing that part of the duty cycle in which strip heater 84 is required to be turned on to keep the temperature of detector unit 38 at the selected level.

This calculated information is employed to generate a high state output which is applied to the gate of a power field effect transistor 416 through an inverter 418 which buffers the digital signal. This turns transistor 416 on, connecting heater 84 across a plus 5 volt operating source to ground.

At the end of the time segment $Q_1$ in each duty cycle, the microcomputer output applied to inverter 418 reverts to a low state. This turns transistor 416 off and interrupts the operation of heater 84.

It is important, in conjunction with the foregoing, that heater 84 keep the entire detector unit, rather than just detectors 42 and 183 per se, at the selected temperature (which is preferably on the order of 40° C). This keeps condensation from forming on the exposed surfaces of filters 182 and 184 and interferring with the transmission of the attenuated beam of infrared radiation to the detectors. Also, the keeping of the entire detector unit at a constant temperature eliminates inaccuracies that would potentially be present if the optical filters 182 and 184 instead expanded and contracted as they would tend to do if they were not kept at a constant temperature.

We pointed out above that another major component of the system illustrated in FIG. 9 is the circuit 230 employed to apply a negative bias to lead selenide infrared radiation detectors 42 and 183 and thereby improve the signal-to-noise ratios of those detectors. This circuit, shown in detail in FIG. 14, includes a flyback transformer T420, a power field effect transistor 422, a secondary diode 424, a storage capacitor C426, and a voltage control circuit 427 which includes operational amplifiers 428 and 430 and a series pass connected field effect transistor 432.

Figure 14:
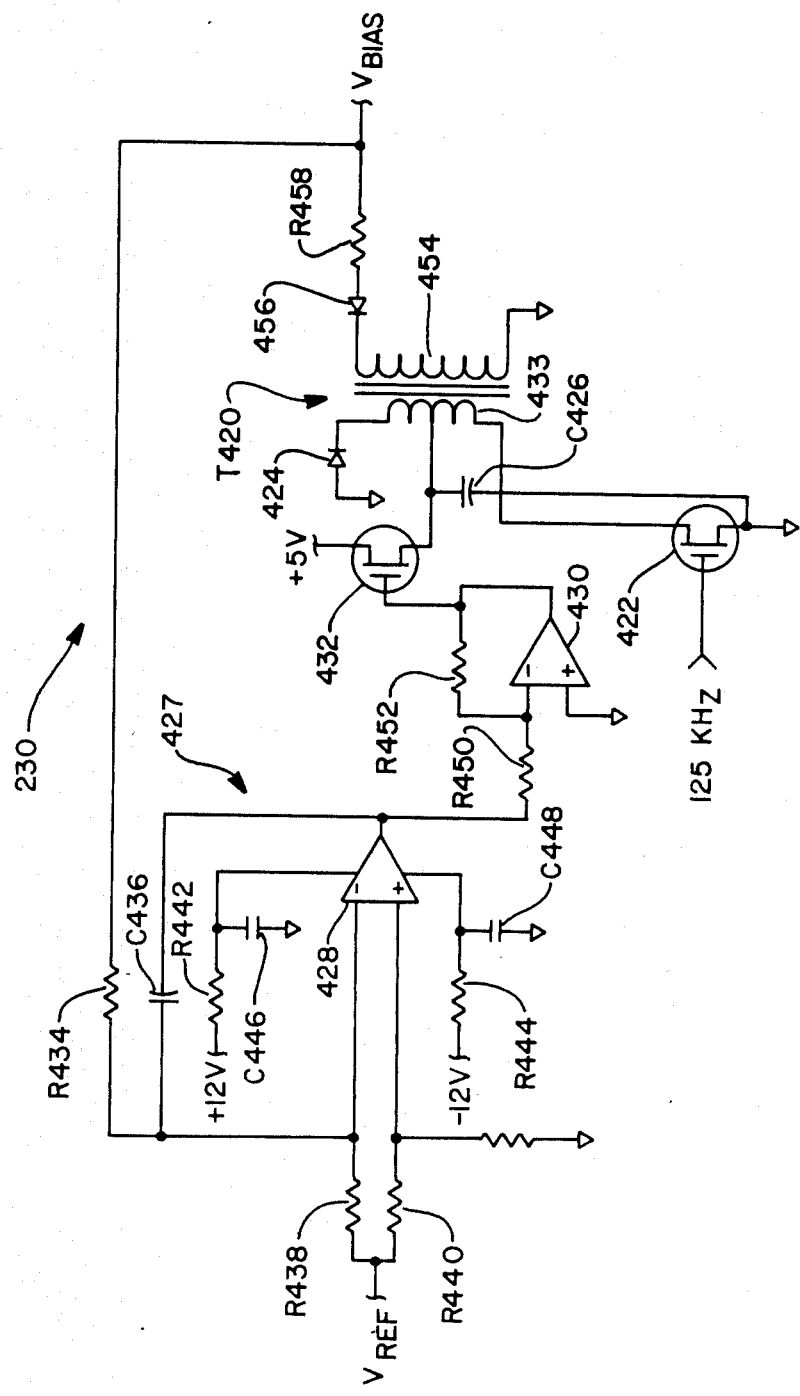
FIG. 14 is a schematic of a circuit employed in the gas analyzer of FIG. 1 to apply an electrical bias to the infrared radiation detectors and thereby improve the signal-to-noise ratio of those detectors.

As shown in FIG. 14, one terminal of transformer primary winding 433 is connected to ground through diode 424, and the other end of that winding is connected to the drain of field effect transistor 422. The control voltage generated by circuit 427 is applied to the center tap of winding 433.

The gate of field effect transistor 422 is supplied with a 125 kHz signal from clock timing generator 226.

When the clock signal goes high, field effect transistor 422 is turned on; and current builds up in transformer primary winding 433. Then, when the clock signal goes low, turning off field effect transistor switch 422, the energy in the magnetic field of transformer T420 causes the voltage in primary winding 433 to fly back to approximately 100 volts. This creates a current in winding 433 which is stored in capacitor C426.

The negative voltage generated when field effect transistor 422 turns off is sensed by a resistor R434 which is connected to the inverting terminal of operational amplifier 428. This resistor is also connected through a capacitor C436 to the output terminal of operational amplifier 428 to form an integrating circuit. This circuit integrates the error between the current flowing through resistor R434 and a reference current developed from reference voltage $V_{REF}$. The reference voltage is supplied by resistor R438, and it is also applied to the inverting terminal of operational amplifier 428.

A second and equal reference current is developed from reference voltage $V_{REF}$ by resistor R440 and applied to the non-inverting terminal of amplifier 428.

The operational amplifier circuit also includes resistors R442 and R444, which provide local isolation, and capacitors C446 and C448 which provide local filtering.

As suggested above, it is the function of the operational amplifier circuit just described to integrate the error between the reference current and the current derived from the reference voltage.

The integrated error current is inverted by unity gain operational amplifier 430. The error signal is applied to the inverting terminal of that amplifier through a resistor R450, which provides amplifier input resistance; and the non-inverting terminal of that amplifier is connected to ground. A resistor R452 connected between the inverting input and the output of amplifier 430 controls the amplifier gain.

The output of operational amplifier 430 is applied to the gate of field effect transistor 432. Consequently, as the error signal increases in magnitude, field effect transistor 432 is turned on to an extent determined by the magnitude of the error current. This controls the voltage across the primary winding 433 of transformer T420 and, consequentially, the voltage across the secondary winding 454 of that transformer, maintaining the latter at the wanted, typically −100 volt level.

A diode 456 and a resistor R458 are connected in series in the biasing voltage supplying secondary winding 454 to provide isolation and rectification, respectively.

In the foregoing circuit, the biasing is typically modulated at a frequency of 125 kHz in order to reduce size of the magnetic and filtering components.

Gas analyzers embodying the principles of the present invention do not have to be of the particular character discussed above. For example, additional detectors may be incorporated to measure the concentration of other gases present in the mixture being analyzed, and hand-held unit 22 and the routines appearing in Appendix A may be modified to provide appropriate displays of the additional information provided by those detectors.

Another modification that can be made within the principles discussed above is to modulate infrared radiation emitting source 36 with A.C. as opposed to the disclosed D.C. electrical voltage. This has the potential advantage of reducing the current density at the interfaces between the radiation emitting layer 162 and the conductors 156 and 158 of an infrared radiation emitter such as that identified by reference character 36 in FIG. 4. That would further reduce the potential for burnthrough attributable to current densities which are too high and would also allow higher current densities to be employed in applications where that is deemed desirable.

Options for eliminating the effect of foreign substances in the optical path between the infrared radiation emitter and infrared radiation detector and the effect of minor instabilities in the latter also exist. For example, two emitters, each filtered to pass only infrared radiation in a specific band, could be employed; and the second, reference emitter could be a diode with a specific spectral output rather than an emitter of the type disclosed here.

A second option would be to substitute for one or both of the disclosed lead selenide detectors a PIN diode or a thermopile detector.

Furthermore, it will be obvious to those skilled in the arts to which this invention relates that gas analyzers as disclosed herein can be incorporated in equipment designed to monitor a variety of functions rather than being constructed as a stand-alone unit.

In addition, instruments employing the principles of the present invention can be employed to measure gases other than carbon dioxide simply by using a different filter to change the wavelength of the detected infrared radiation. And, the mixture being analyzed may be of an industrial origin, as an example, rather than the gases breathed out by a medical patient.

From the foregoing, it will be apparent to the reader that our invention may be embodied in many specific forms in addition to those disclosed above without departing from the spirit or essential characteristics of the invention. The embodiments of the invention disclosed herein are therefore to be considered in all respects as illustrative and not restrictive. The scope of the invention is instead indicated by the appended claims, and all changes which come within the meaning and range of the equivalency of the claims are therefore intended to be embraced therein.

What is claimed as the invention is:

1. A device for emitting modulated infrared energy in a stable, repeatable manner, said device comprising: a non-metallic substrate fabricated of a material possessing low thermal conductivity; a layer of an emissive, electrically resistive material on said substrate; and means for applying pulses of electrical energy across said layer of emissive, electrically resistive material to periodically produce the wanted emission of infrared energy therfrom, the means for applying said pulses across said emissive layer comprising an operatioonal amplifier, electronic switch means for so applying a signal to one input of said operational amplifier as to cause a signal to appear at the output of said operational amplifier, means responsive to the appearance of said output signal to connect said emissive layer across two power sources of equal magnitude but opposite polarity, and a differential resistor network for precisely controlling the voltage thus applied across said emissive layer, said differential resistor network comprising one pair of resistors connected in series between one side of said emissive layer and ground and a second pair of resistors connected in series between the other side of said emissive layer and a lead routing the input signal to said operational amplifier, the resistors in one of said pairs being matched to the resistors in the other of said pairs.

2. A device for emitting modulated infrared energy as defined in claim 1 in which the substrate has a thermal conductivity which is approximately one order of magnitude lower than the thermal conductivity of alumina and the thermal properties of the substrate and the thermal properties of said electrically resistive material are so related as to enable said electrically resistive material to efficiently emit infrared energy at a high energy level, at a frequency in the range of 40 to 100 Hz, with a high signal-to-noise ratio, and with a sharktooth waveform when electrical energy is applied to said emissive, electrically resistive material.

3. A device for emitting modulated infrared energy as defined in claim 1 in which the substrate is made of steatite.

4. A device for emitting modulated infrared energy as defined in claim 3 in which the substrate is in the range of 0.0025 to 0.0035 inch thick.

5. A device for emitting modulated infrared energy as defined in claim 1 which also includes first and second electrical conductors for electrically connecting said one pair of resistors and said second pair of resistors in series with said layer of electrically resistive material, each of said conductors being a film of conductive material adhered to said substrate and interposed between said substrate and said layer of electrically resistive material and on the order of at least 50 percent of said layer of electrically resistive material overlapping said electrical conductors.

6. A device for emitting modulated infrared energy as defined in claim 5 wherein said conductors are fabricated of a gold platinum alloy.

7. A device for emitting modulated infrared energy as defined in claim 5 wherein said conductors have integral arms and stems arranged in a T-shaped configuration and are bonded to said substrate with the arms of the two conductors in spaced apart relationship.

8. A device for emitting modulated infrared energy as defined in claim 1 wherein said layer of electrically resistive material is the reaction product obtained by firing an ink theretofore applied to said substrate.

9. A device for emitting modulated infrared energy as defined in claim 1 which includes a thin film of essentially pure platinum metal superimposed on said layer of electrically resistive material to increase the emissivity of the device.

10. A device for emitting modulated infrared energy as defined in claim 9 wherein said film of platinum metal is on the order of 10 to 200 angstroms thick.

11. A device for emitting infrared energy in a stable, repeatable manner, said device comprising: a non-metallic substrate fabricated of a material possessing a thermal conductivity which is approximately one order of magnitude lower than the thermal conductivity of alumina; a layer of an emissive, electrically resistive material on said substrate; and means for applying electrical energy to said emissive, electrically resistive material to produce the wanted emission of infrared energy therefrom; the thermal properties of said substrate and the thermal properties of said emissive, electrically resistive material being so related as to enable said device to efficiently emit infrared radiation at a high energy level, at a frequency in the range of 40 to 100 Hz, with a high signal-to-noise ratio, and with a sharktooth waveform when electrical energy is applied to said emissive, electrically resistive material and said device further comprising a thin film of essentially pure platinum metal superimposed on said layer of electrically resistive material to thereby increase the emissivity of said infrared radiation emitter.

12. A device for emitting infrared energy as defined in claim 11 wherein said film of platinum is on the order of 10 to 200 angstroms thick.

13. A device for emitting infrared energy in a stable, repeatable manner, said device comprising: a non-metallic substrate fabricated of a material possessing a thermal conductivity which is approximately one order of magnitude lower than the thermal conductivity of alumina; a layer of an emissive, electrically resistive material on one surface of said substrate; and means for applying electrical energy to said emissive, electrically resistive material to produce the wanted emission of infrared energy therefrom; the thermal properties of said substrate and the thermal properties of said emissive, electrically resistive material being so related as to enable said device to efficiently emit infrared energy at a high energy level, at a frequency in the range of 40 to 100 Hz, with a high signal-to-noise ratio, and with a sharktooth waveform when electrical energy is applied to said emissive, electrically resistive material; the means for applying electrical energy to said electrically resistive material including first and second, spaced apart conductors bonded to said one surface of said substrate; said first and second conductors having integral arms and stems arranged in a T-shaped configuration and being bonded to said one surface of said substrate with the arms of said conductors in spaced apart relationship; and said layer of electrically resistive material spanning the gap between, overlapping, and being electrically connected at the opposite ends thereof to the arms of said first and second conductors, whereby said electrically resistive material can be heated to effect the wanted emission of infrared energy therefrom by applying a differential voltage across said first and second conductors.

14. A device for emitting infrared energy in a stable, repeatable manner, said device comprising: a non-metallic substrate fabricated of a material possessing a thermal conductivity which is approximately one order of magnitude less than the thermal conductivity of alumina; a layer of an emissive, electrically resistive material on said substrate; and means for applying electrical energy to said emissive, electrically resistive material to produce the wanted emission of infrared energy therefrom; the thermal properties of said substrate and the thermal properties of said emissive, electrically resistive material being so related as to enable said material to efficiently emit infrared energy at a high energy level, at a frequency in the range of 40 to 100 Hz, with a high signal-to-noise ratio, and with a sharktooth waveform when electrical energy is applied to said emissive, electrically resistive material and said device also including first and second, spaced apart conductors bonded to said substrate; said electrically resistive material spanning the gap between, and overlapping onto, said conductors, whereby said electrically resistive material can be heated to effect the controlled emission of infrared energy therfrom by applying a differential voltage across said first and second conductors; and said layer of emissive, electrically resistive material being the reaction product obtained by firing an ink theretofore applied to said substrate.

15. A device for emitting infrared energy as defined in any of the preceding claims 11, 13, or 14 in which said substrate is made of steatite.

16. A device for emitting infrared energy as defined in claim 13 or in claim 14 wherein each of said first and second conductors is a film of conductive material adhered to said substrate and interposed between said substrate and said layer of electrically resistive material and on the order of at least 50 percent of said layer of electrically resistive material overlaps said conductors.

17. A device for emitting infrared energy as defined in claim 11 which includes first and second, spaced apart conductors bonded to said substrate; said electrically resistive material spanning the gap between, and overlapping onto, said conductors, whereby said electrically resistive material can be heated to effect the controlled emission of infrared energy therefrom by applying a differential voltage across said first and second conductors; said first and second conductors each having a film of conductive material adhered to said substrate and interposed between said substrate and said layer of electrically resistive material; and on the order of at least 50 percent of said layer of electrically resistive material overlapping said conductors.

18. A device for emitting infrared energy as defined in any of the preceding claims 13, 14, or 17 in which the conductors are fabricated of a gold platinum alloy.

19. A device for emitting infrared energy as defined in claim 14 or in claim 17 wherein said conductors have integral arms and stems arranged in a T-shaped configuration and are bonded to said substrate with the arms of the two conductors in spaced apart relationship.

20. A device for emitting infrared energy as defined in claim 15 in which the substrate is in the range of 0.0025 to 0.0035 inch thick.

* * * * *